United States Patent
De Rosa et al.

(10) Patent No.: US 10,206,944 B2
(45) Date of Patent: Feb. 19, 2019

(54) CHONDROITIN FOR USE IN MEDICINE

(71) Applicant: ALTERGON S.A., Lugano (CH)

(72) Inventors: Mario De Rosa, Lugano (CH); Chiara Schiraldi, Lugano (CH)

(73) Assignee: ALTERGON S.A., Lugano (CH)

( * ) Notice: Subject to any disclaimer, the term of this patent is extended or adjusted under 35 U.S.C. 154(b) by 835 days.

(21) Appl. No.: 14/400,069

(22) PCT Filed: May 22, 2013

(86) PCT No.: PCT/EP2013/060501
§ 371 (c)(1),
(2) Date: Nov. 10, 2014

(87) PCT Pub. No.: WO2013/174863
PCT Pub. Date: Nov. 28, 2013

(65) Prior Publication Data
US 2015/0258134 A1    Sep. 17, 2015

(30) Foreign Application Priority Data

May 23, 2012 (IT) .............................. MI2012A0896

(51) Int. Cl.
*A01N 43/04* (2006.01)
*A61K 31/715* (2006.01)
*A61K 31/726* (2006.01)

(52) U.S. Cl.
CPC .......... *A61K 31/726* (2013.01); *A61K 31/715* (2013.01)

(58) Field of Classification Search
None
See application file for complete search history.

(56) References Cited

U.S. PATENT DOCUMENTS 5,587,363 A * 12/1996 Henderson ......... A61K 31/7008
514/54

FOREIGN PATENT DOCUMENTS

WO    WO01/80810    11/2001

OTHER PUBLICATIONS

Campo et al. Free Radic. Res. (2003), vol. 37, pp. 257-268.*
Adams et al. Biochem. J. (1981), vol. 197, pp. 385-389.*
Cole et al. The American Journal of Sports Medicine (2006), vol. 34, pp. 919-927.*
Sakko, et al., "Immonohistochemical Level of Unsulfated Chondroitin Disaccharides in the Cancer Stroma is an Independent Predictor of Prostate Cancer Relapse", Cancer Epidemiol Biomarkers Prev 2008; 17(9), Sep. 2008.
Kujawa et al., "Hyaluronic Acid Bonded to Cell-Culture Surfaces Stimulates Chondrogenesis in Stage 24 Limb Mesenchyme Cell Cultures", Developmental Biology 114, 504-508 (1986).
Kujawa et al., "Substrate-Bonded Hyaluronic Acid Exhibits a Size-Dependent Stimulation of Chondrogenic Differentiation of Stage 24 Limb Mesenchymal Cells in Culture", Developmental Biology 114, 519-528 (1986).
International Search Report and Written Opinion of corresponding International case PCT/EP2013/060501 dated Aug. 28, 2013.

* cited by examiner

*Primary Examiner* — Patrick T Lewis
(74) *Attorney, Agent, or Firm* — Silvia Salvadori, P.C.; Silvia Salvadori

(57) ABSTRACT

Chondroitin, a metabolic intermediate of chondroitin sulphate biosynthesis in mammals and other living organisms, possesses biological properties different from those of chondroitin sulphate, and can be advantageously used for applications in the pharmaceutical, nutraceutical, cosmeceutical and medical device fields. Chondroitin has biostimulating, anti-inflammatory and anti-microbial activity and can be used in the treatment of osteoarthritis, eye disorders, interstitial cystitis, lung disorders, inflammatory disorders in general, oncological disorders, peritoneal dialysis, tissue biorevitalisation and wound repair, as a skin filler, and as bioresorbable scaffolds.

4 Claims, No Drawings
Specification includes a Sequence Listing.

CHONDROITIN FOR USE IN MEDICINE

This application is a U.S. national stage of PCT/EP2013/060501 filed on May 22, 2013, which claims priority to and the benefit of Italian Application No. MI2012A000896 filed on May 23, 2012, the contents of which are incorporated herein by reference in their entireties.

The present invention relates to pharmaceutical, nutraceutical and cosmeceutical compositions or medical devices containing non-sulphated chondroitin as active ingredient.

PRIOR ART

Chondroitin, the metabolic precursor of chondroitin sulphate, is a natural linear polysaccharide formed by alternating residues of N-acetyl-D-galactosamine β 1:4 and D-glucuronate β 1:3. In vertebrates, chondroitin is sulphated regioselectively at the 4 or 6 hydroxyls of N-acetyl-D-galactosamine, and in some cases the 2 or 3 hydroxyls of glucuronic acid (Sugahara et al., J. Biol. Chem., 1996, 271:26745-54). The molecular weight of chondroitin, and the extent and sites of sulphation, depend on species, age and tissue type (Kuettner et al., Eds., in Articular cartilage and osteoarthritis, NY, Raven Press, 1992; Volpi Ed., in Chondroitin sulfate: structure, role and pharmacological activity, S. Diego, Calif. Academic Press—Elsevier Inc, 2006).

Chondroitin sulphate, which represents the polysaccharide part of various families of proteoglycans (GAGs), is bonded to a serine residue of the core protein via the tetrasaccharide GlcA-Gal-Gal-Xyl. As for the majority of membrane proteins, the biosynthesis of the core protein of the GAGs starts in the cytosol, and the polypeptide then translocates to the endoplasmic reticulum. Tetrasaccharide synthesis begins in the lumen of the endoplasmic reticulum and is completed in the golgi, where polymerisation/sulphation of chondroitin sulphate begins. Polymerisation takes place due to the concerted, highly organised action of a multienzyme system associated with the membrane, wherein GalNAc transferase and GlcA transferase add the two sugars alternately at the non-reducing extremity of the nascent proteoglycan, leading to the formation of chondroitin chains of about 70 kDa. The sulphation of the polymer takes place in the golgi; in particular, sulphation in the 6-position takes place in the medial/trans region of the golgi, while sulphation in the 4-position takes place in the trans region. Studies with microsomal preparations (Sugumaran and Silbert, J. Biol. Chem. 1990, October 25, 265(30):18284-8) have demonstrated that the sulphation process begins only 30 seconds after the start of the chondroitin polymerisation process; in the sulphation process the donor substrate of the sulphate group is PAPS (3'-phosphoadenosine 5'-phosphosulphate), the formation of which is catalysed by ATP sulphurylase and APS kinase.

The activation reaction of the sugars and sulphate takes place in the cytosol; the forms activated are then transported to the endoplasmic reticulum and the golgi, where they are used for the synthesis of chondroitin sulphate.

The GAGs in the extracellular matrix take on very extensive conformations, forming porous gels to which cations and water are attracted. In this way the GAGs hydrate and expand the tissues, making the matrix suitable to withstand even strong compressive forces.

Chondroitin sulphate is not only present in vertebrates, but also in zebra fish, nematodes and insects. Some bacteria also produce polymers correlated with chondroitin as components of their capsules. Unlike vertebrates, these polysaccharides are not present as proteoglycans and are not sulphated, but are associated with the lipid components of the bacterial surface or are released into the culture medium (Whitfield, Ann. Rev. Biochem. 2006, 75:39-68; DeAngelis, Glycobiol, 12:9R-16R).

Chondroitin sulphate, obtained by extraction from various animal sources, such as pig cartilage, shark's fin and teleost cartilage, is used as a nutraceutical and as a chondroprotective and anti-rheumatic medicament in the treatment of tibiofibular osteoarthritis of the knee and in osteoarthritis of the joint cartilage (Kuettner K E et al., Eds., in Articular cartilage and osteoarthritis, NY, Raven Press, 1992; Simànek V et al., 2005, 149:51-56; Goerres G W et al., J. Clinical Densitometry 2005, 8:484-487; Altman R D et al., OsteoArthritis and Cartilage 2005, 13:13-19; Chan P S, et al., OsteoArthritis and Cartilage 2005, 13:387-394; Chou M M, et al., Exp. Biol. Med. 2005, 230:255-262; Clegg D O, et al., New England J. of Medicine, 2006, 23:795-808; Roman-Blas et al., OsteoArthritis and Cartilage, 2006, 14:839-848; Maheu E et al., OsteoArthritis and Cartilage, 2006, 14:303-322; Fotinì N et al., Biomed. Chromatogr. 2006, 20:539-550; Lagnaoui R et al., Thérapie 2006, 61: 341-346; Volpi N Ed. in Chondroitin sulfate: structure, role and pharmacological activity, S. Diego, Calif. Academic Press—Elsevier Inc, 2006; Zhang W et al., Ann. Rheum. Dis. 2007, 66:377-38. Other therapeutic fields in which chondroitin sulphate is used are interstitial cystitis (Nickel et al., BJU Int. 2009, 103:56-60; Cervigni et al., Int Urogynecol. J. Pelvic Floor Dysfunction. 2008, 19:943-947) and synovitis (Hochberg and Clegg, Osteoarthritis and Cartilage 2008, 16 supp. 3:S22-S24; Moller, Osteoarthritis and Cartilage 2009, 17 supp. 1:S32-S33).

However, chondroitin, a metabolic intermediate, cannot be isolated in significant quantities from animal sources. Processes for the production of chondroitin from microorganisms or by enzymatic synthesis were only devised recently.

The production of chondroitin by an engineered strain of E. coli K4, described in WO 2010136435, is particularly interesting; said strain produces polysaccharide K4, a chondroitin which presents β-fructofuranose residues in C3 of glucuronic acid. These residues can easily be removed by controlled acid hydrolysis, due to the low stability of the glycoside bond with which the fructose is bonded to the chondroitin chain. The engineering of the strain was designed to improve the processivity of the entire enzyme complex responsible for the synthesis of polysaccharide K4 by inserting several copies of the autologous gene Rah, which acts as positive regulator of the transcription of the cluster of genes responsible for synthesis of capsular material. Using this micro-organism and an integrated strategy based on optimisation of a three-phase fermentation process (batch—fed batch—in microfiltration regimen), chondroitin yields >8 g/L are obtained. The high production yields, the simplicity of the downstream purification process, low overall process costs and low environmental impact make the process described in WO 2010136435 superior to all the fermentation strategies previously described (Rodriguez et al., Eur. J. Biochem., 1988, 177:117-124; Manzoni et al., Biotechnology Letters, 1996, 18:383-386; WO 01/02597 A1; U.S. Pat. Nos. 6,288,044; and 6,777,398; US 2005266460; WO 0180810; EP 1282684; EP 1832662; US 20030104601; US 20050164984; US 20070015249; US 20030109693; EP 1950308; WO 2007145197; WO 2007069693; WO 2007058252; WO 2007058252; WO 2007023867; U.S. Pat. No. 7,273,729; JP 2004024208; US 20060052335; US 20060057697; U.S. Pat. No. 7,232,676; US 20070059805). More recently, US 2011244520A1 described a series of engineered micro-organisms which produce chondroitin in concentrations comparable with those of WO 2010136435.

As regards the enzymatic synthesis of chondroitin, US 2005266460, WO 0180810, EP 1282684, EP 1832662, US 20030104601 and US 20050164984 disclose the use of chondroitin synthetase from *Pasteurella multocida*, an enzyme that catalyses the synthesis of chondroitin from the corresponding UDP sugars. In particular, these documents describe the sequence of the nucleotide segment encoding for the enzyme, the construction and use of recombinants (in prokaryotic and eukaryotic expression systems) which express them, and the production of modified chondroitin of various dimensions with said recombinants. All these documents lack experimental evidence of the production processes claimed; in particular, detailed data about the fermentation methods used to produce the enzymes, and the chondroitin yields, are never reported. US 20070015249 and US 20030109693 describe the production of a chondroitin synthetase from *E. coli* K4 and its use for the production of chondroitin in vitro. The production of the enzyme, encoded by the kfoC gene of region II of the *E. coli* K4 cluster responsible for biosynthesis of the capsular antigen, is characterised by the following stages: amplification of kfoC, cloning of the gene in the pTrcHis vector, and its expression in the commercial strain of *E. coli* TOP. The two documents also claim natural or artificial proteins with mutations, which can induce slight structural modifications in chondroitin synthetase without altering its catalytic function. These documents also lack data about the yields of the production processes, regarding the production of chondroitin synthetase and the enzymatic production of chondroitin in vitro from the corresponding UDP-sugars.

EP 1950308, WO 2007145197, WO 2007069693, WO 2007058252, WO 2007058252 and WO 2007023867 describe in vitro methods of synthesising chondroitin and derivatives which use chondroitin synthetase from *E. coli* K4 and mutants thereof, which only have one of the two transferase activities.

U.S. Pat. No. 7,273,729, JP 2004024208, US 20060052335, US 20060057697 and U.S. Pat. No. 7,232,676 disclose the use of human chondroitin synthetase, an enzyme that catalyses the synthesis of chondroitin from the corresponding UDP sugars. The documents claim the structure of human chondroitin synthetase, an expression vector which comprises the sequence of the enzyme, the expression of said vector in eukaryotic cells, and a method for synthesising the polysaccharide chain of chondroitin.

US 20070059805 claims the structure of human chondroitin synthetase, an expression vector which comprises the sequence of the enzyme, the expression of said vector in eukaryotic cells, and a method for synthesising the polysaccharide chain of chondroitin.

All the documents cited above consider chondroitin to be an intermediate for chondroitin sulphate synthesis, without indicating its intrinsic biological properties. Some of them do mention the possibility of using chondroitin in unspecified compositions, but only generically, as in the case of US 20110244520 (claim 63) and WO 0180810 (claim 73); this last document states on pp. 4-5 that chondroitin polymers are "more inert, loosely speaking, than the analogous HA molecule". Kujawa M J et al., (Developmental Biology 1985, 114, 504-518 and 519-528) describe that hyaluronic acid and, albeit less efficiently, chondroitin, stimulate in vitro chondrogenesis of stage 24 chick limb mesenchymal cells in culture (4.5 days after fertilization). This effect is only observed when said polysaccharides are covalently bonded to the surfaces on which cells are cultured, while no effects are observed when such molecules are in solution. No therapeutic applications can be connected with such observations, which relate to the ambyogenesis process under stringent conditions in an experimental model that cannot be generally applicable.

WO 2012/032151 also describes hybrid cooperative complexes between hyaluronic acid and chondroitin. The latter is only proposed as a rheological excipient to reduce viscosity, and no pharmacological effect is described.

DEFINITIONS

The term chondroitin is often used improperly to indicate chondroitin sulphate; for the sake of clarity, therefore, the two terms "chondroitin" and "chondroitin sulphate" will be used separately hereafter. The term "chondroitin" means the non-sulphated polysaccharide, indicated by the letter C, while the term "chondroitin sulphate" means the differently sulphated polysaccharide, indicated by the letters CS.

DESCRIPTION OF THE INVENTION

While the use of chondroitin sulphate in the medical field is extensively documented, no data are yet available for applications of chondroitin. It has now been discovered that chondroitin possesses a series of important biological activities which make it useful for various applications not only in the therapeutic field, but also in aesthetic medicine, nutraceuticals and cosmeceuticals.

Experimental models and clinical trials have demonstrated that chondroitin interacts with biological systems in a multifactorial way, giving rise to biological responses in the cells, tissues and the entire body which are novel or greater than those of chondroitin sulphate.

Although chondroitin is a metabolic intermediate for the biosynthesis of chondroitin sulphate, said molecule is not present as such in the tissues, because it is already anchored at the biosynthesis stage to a serine residue of the core protein via the tetrasaccharide GlcA-Gal-Gal-Xyl, on which the chain formed by the repetition of the disaccharide units of N-acetyl-D-galactosamine β 1:4 and D-glucuronate β 1:3 grows. The process of elongation of the chain, and its subsequent sulphation, take place almost simultaneously.

The presence of free chondroitin in the body following exogenous administration therefore represents a new metabolic condition, responsible for a series of multifactorial biological responses.

It has been found that chondroitin stimulates cell growth, in particular growth of the chondrocytes, promoting the maintenance of the cell type, possesses anti-inflammatory and antibacterial activity, and stimulates wound repair. Chondroitin can also advantageously replace chondroitin sulphate or other glycosaminoglycans in the applications typical of the latter, for example in viscosupplementation, cartilage repair, in the ophthalmic field, in the treatment of joint disease, and in skin biorevitalisation treatments using intradermal microinjections. It has also been found that chondroitin boosts the activity of antitumoral active constituents and is useful in the treatment of various disorders such as osteoarthritis, interstitial cystitis, and disorders of the respiratory system. Chondroitin is also useful in peritoneal dialysis solutions and as a structural component of tissue growth scaffolds.

The invention therefore relates to pharmaceutical, nutraceutical and cosmeceutical compositions or medical devices containing non-sulphated chondroitin as active ingredient.

Chondroitin can optionally be combined with other active ingredients, such as hyaluronic acid, anti-inflammatories, antitumoral drugs, mucolytics and antibacterials.

The administration routes and doses will depend on the type of condition to be treated, and can be established by experts on the basis of pre-clinical and clinical studies, using known methodologies. Broadly speaking, the doses will not be substantially similar to those currently used for chondroitin sulphate when employed in the same applications. Said doses can be, for example, between 0.1 and 200 mg/Kg orally and between 0.01 and 20 mg/Kg by injection, while the topical formulations can contain chondroitin concentrations ranging between 0.01 and 80% by weight. Chondroitin can be formulated in compositions suitable for oral, injectable or topical administration. Examples of these forms of administration include capsules, tablets, eyedrops, gels, creams, solutions or suspensions, orodispersible powders, sprays and syrups.

The injectable, oral or topical administration of chondroitin, even at very high doses, does not cause adverse reactions which may prejudice its use. The toxicological characteristics of chondroitin, reported in Table 1, demonstrate its safety.

DETAILED DESCRIPTION OF THE INVENTION

The experimental evidence forming the basis of the uses to which the invention relates is summarised below. Further details are reported in the examples.

Stimulation of Cell Growth

The presence of chondroitin strongly stimulates the growth of numerous cell types, such as keratinocytes, fibroblasts and, in particular, chondrocytes. A complex phenomenology is involved, clearly demonstrated by in vitro experiments that simulate the wound-healing process. The wound-healing experiments are conducted by time-lapse optical microscopy, a technique that allows cell behaviour to be monitored for lengthy times (2-4 days) in terms of adhesion, proliferation and motility, in an environment that reproduces the optimum conditions for cell growth (atmosphere with 5% v/v of $CO_2$ in humid air and temperature of $37\pm0.1°$ C.). The culture is grown to confluency and a cut (wound) is made in it; the rate of repair is then evaluated over time by calculating the variation in the area of the wound. Qualitative and quantitative analysis shows that wound repair in the presence of chondroitin takes less than 20 h, whereas in the

TABLE 1

Toxicological profile of chondroitin; the experimental details are reported in Examples 5-9.

| Test | Experimental model | Values |
|---|---|---|
| Toxicity | | |
| Acute | Mouse/rat | $LD_{50}$ >2000 mg/Kg p.o. and 160 mg/Kg i.v. |
| Subacute 30 days | Rat | No toxicity >200 mg/kg/day p.o. and i.m. |
| Chronic 26 weeks | Rat | No toxicity >200 mg/kg/day p.o. |
| Mutagenicity/genotoxicity | | |
| In vitro test, Ames' test | 5 strains of *Salmonella typhimurium* | Up to 2.0 mg/plate: no point-reverse mutation |
| In vitro test, chromosomal aberration test | Human lymphocytes | Up to 5 µg/mL no significant increases in the number of cells bearing chromosomal aberrations are observed, |
| In vitro test, DNA-repair test | *Escherichia coli* strain sensitive to the action of mutagenic sub stances | Even at higher doses it does not interact and does not alter the DNA |
| In vivo test, micronucleus test | Mouse | Even at the dose of 80 mg/Kg, chondroitin can be considered non-mutagenic in the early micronucleus test |
| Carcinogenicity study | Rat | Histopathological examination of the subchronic and chronic tests conducted on the rat demonstrates the total absence of potential neoplastic degeneration in all the fundamental organs. |
| Toxicity studies on the reproductive system | | |
| Study of fertility and reproductive capacity | Rat | Daily oral administration of chondroitin for 60 days, even at the dose of 200 mg/Kg, has no effect on the fertility of male rats. Similarly, daily administration of up to 200 mg/Kg for 15 days before mating and up to the 21st day of lactation has no effect on the reproductive capacity of the females |
| Study of embryo-foetal development | Rat | Chondroitin does not present teratogenic activity, even at the maximum dose tested of 100 mg/Kg |
| Study of postnatal development | Rat | Chondroitin does not have teratogenic effects in rats after the administration of an oral dose of 200 mg/Kg/day from the 15th day of gestation to the end of the lactation period. |
| Sensitisation | | |
| Systemic sensitisation and anaphylaxis | Guinea pig | Chondroitin does not induce anaphylactic or hypersensitivity reactions in any of the animals treated |
| Skin sensitisation | Guinea pig | No sign of skin sensitisation can be observed in the treated animals. | presence of chondroitin sulphate the wound does not heal completely, even after 70 h; under the same conditions, the control (medium without added polysaccharide) closes after 40 h. In each of the experimental conditions, C exhibits the ability to reduce healing time, which is approximately halved. This result represents an important indicator of healing of open wounds, consequently reducing the typical complications relating to infections, sepsis, etc.

Stimulation of Chondrocyte Growth and Maintenance of Cell Type

The experiment on primary cultures of human chondrocytes, isolated from samples of healthy human cartilage obtained during rhinoplasty operations, demonstrates that the presence of chondroitin in the culture medium not only stimulates cell growth, but also has a specific action in maintaining the chondrocyte cell type. In the case of chondrocytes a process of cell differentiation is observed which, as the growth phases proceed, have an appearance increasingly morphologically similar to fibroblasts. This type of behaviour is counteracted by the presence of chondroitin in the culture medium. A study of the effect of chondroitin on chondrocyte proliferation, conducted with time-lapse videomicroscopy, shows that the growth of cells treated with chondroitin is better than that of untreated cells and cells treated with chondroitin sulphate.

Phenotype analysis involving immunohistochemical tests on human chondrocytes grown in the presence of chondroitin or chondroitin sulphate shows that after 4 days' treatment the different cultures (untreated cells, cells treated with chondroitin and cells treated with chondroitin sulphate) all present strong positivity to type II collagen, a specific marker for the chondrocyte cell type, but this condition is only maintained for longer times (7 and 10 days) in the cells treated with chondroitin.

Real-time PCR analysis of the gene expression of the main specific differentiation markers (β-actin, aggrecan, type II collagen, type I collagen and sox9) in human chondrocytes grown in the presence of chondroitin or chondroitin sulphate shows that: a) treatment with chondroitin causes a variation in expression of the differentiation and matrix genes analysed (aggrecan, type I collagen, type II collagen and sox9) at the different analysis times considered (4, 7 and 10 days); b) if the chondrocytes in the second growth phase are treated with chondroitin, they present high levels of expression of type II collagen, whereas if they are treated with chondroitin sulphate, they present high levels of expression of type I collagen, accompanied by an evident morphological change in fibroblast type; c) the cells in the third growth phase present a lower response to treatment with chondroitin or chondroitin sulphate, although persistence of expression of type II collagen in the presence of chondroitin is clearly observed, demonstrating the maintenance of the chondrocyte phenotype even in advanced growth phases.

These results have considerable application interest in tissue engineering, demonstrating that the chondrocyte growth obtainable by transplantation in the presence of chondroitin allows the cells to be amplified over time, maintaining the chondrocyte phenotype and therefore the characteristics of the tissue which is being formed. This result is also important in pharmacological terms for the use of chondroitin in all disorders wherein the chondrocyte phenotype and its optimum metabolism play a strategic role in curing the disorder.

Anti-Inflammatory Activity

The use of chondroitin sulphate in the treatment of osteoarthritis (OA) was based for decades on the hypothesis that its content declines with age in patients suffering from OA, and that the product administered consequently has the function of supplementing the reduced biosynthesis capacity of the proteoglycans and synovial fluid. Recent studies of the action mechanisms of chondroitin sulphate in the treatment of OA have modified this action mechanism hypothesis, demonstrating that chondroitin sulphate is actively involved in reducing the inflammatory state underlying the progression of OA and rheumatoid arthritis. In particular, it has been demonstrated that as a result of repeated joint traumas (cartilage tissue, synovial fluid, subchondral bone) pro-inflammatory mediators, which play a crucial role in the pathogenesis of the disorder, are released into the extracellular matrix. They include interleukin 1b (IL-1β) and tumour necrosis factor a (TNF-α). In particular, in the chondrocytes, IL-1β bonds to membrane receptors and activates signalling routes via kinases such as ERK-1/2 and p38MAPK, which in turn activate inflammatory pathways in the cell. In particular, in vitro studies have demonstrated that chondroitin sulphate inhibits phosphorylation and activation of ERK-1/2 and p38MAPK, consequently reducing the translocation of NF-kB, which supports an anti-inflammatory effect of chondroitin sulphate (Du Souich, P., et al., J. Cellular and Molecular Medicine, 2009, 13:1451-1463). In a more recent study performed on human chondrocytes extracted from knee cartilage and amplified in the laboratory, Calamia et al. (Calamia V et al., Arthritis Res. Ther., 2010, 12(4):R138) studied the effect of adding IL-1b, a pro-inflammatory cytokine (Fernandes J C, et al., Biorheology, 2002, 39:237-246), and the modulation of two markers involved in the manifestation of the inflammatory state, chaperonin GRP78 and the enzyme superoxide dismutase (SOD-2), was evaluated.

A comparative study between chondroitin and chondroitin sulphate has demonstrated that although chondroitin is a molecule not naturally present in the body, it is able to activate in vitro, on cell systems like chondrocytes, signalling actions of the same type as those proposed for chondroitin sulphate, but significantly more powerful. Experimental results demonstrate that: a) the expression of GRP78 is positively modulated by treatment with chondroitin, to a significantly better extent than chondroitin sulphate; b) the process of up-regulation of SOD-2 induced by IL-1β (a symptom of strong oxidative stress) is effectively reduced by pre-treatment with chondroitin, whereas pre-treatment with chondroitin sulphate is ineffective.

Chondroitin is therefore a medicament useful in the treatment of disorders wherein the inflammatory component is the result or a causal factor of the disorder, as in the case of OA and rheumatoid arthritis.

Antibacterial Activity

It was recently demonstrated that in patients suffering from OA, administration of the antibiotic trimoxazole to treat a concomitant urinary infection also has the effect of significantly alleviating the symptoms of OA. This finding led to the hypothesis that the action of chondroitin sulphate in the treatment of OA may also be associated, at least to some extent, with a possible antimicrobial activity. This hypothesis was borne out by two studies (Rozin A P, Clin. Rheumatol., 2009, October 28(10):1221-3; Sprecher H. et al., Clin. Exp. Rheumatol., 2008, 26(3):509-510) which demonstrate antibacterial activity against *Escherichia coli* by products containing chondroitin sulphate.

A comparative study between chondroitin and chondroitin sulphate demonstrated that although chondroitin is present in the capsule of some micro-organisms in variously modified forms (e.g. fructosylated), it is able to inhibit the growth of pathogenic enterobacteria. In particular, a marked action on *Escherichia coli* and *Enterococcus faecalis* has been demonstrated.

This activity contributes to the efficacy of chondroitin in various indications, such as: a) wound healing, because as well as promoting wound repair, the presence of chondroitin prevents the risk of infection of exposed tissues; b) OA, because altered intestinal/faecal flora has adverse effects on the progression of the disorder, as demonstrated in the literature; the antibacterial effect therefore acts as an adjuvant factor to prevent the disorder from worsening; c) interstitial cystitis, because areas in which fluids stagnate may constitute preferential areas for bacterial infiltration and infections.

Stimulation of Wound Repair

Due to its multiple interactions with the cell systems, chondroitin possesses a considerable ability to accelerate the tissue repair processes. The ability of topical applications of chondroitin or chondroitin sulphate to accelerate the healing process was evaluated on a widely recognised experimental model, the mini-pig. Wounds were made surgically on the back of the animal, and the treatment was performed by slowly dripping the aqueous solution of the compounds into the wound twice a day, and dabbing with a gauze dressing which was then used to cover the wound. The study continued for 6 weeks.

The dermatological evaluation of wound healing demonstrated that the quality of the healing process was better in the presence of chondroitin than chondroitin sulphate, because the former was faster and characterised by a qualitatively better appearance of the wound edges and the surrounding tissue.

In the case of treatment with chondroitin, histopathological evaluation showed a lower content of granulation tissue, and much milder inflammatory symptoms, than in the treatment with chondroitin sulphate.

Histological evaluation demonstrated that in the case of treatment with chondroitin, the organisation of the collagen fibres was similar to that of normal tissue, indicating an advanced wound-healing process.

Treatment of Joint Disorders

The regeneration capacity of chondroitin at cell level, the rheological properties of said polysaccharide and its specific action on the chondrocyte cell type form the basis for the use of this compound in the treatment of joint disease. Evaluation of the therapeutic potential of chondroitin in the treatment of joint disease conducted on the dog, an experimental model wherein degenerative or inflammatory orthopaedic problems associated with degenerative joint disease (DJD) are particularly recurrent at both young and geriatric age, demonstrated that 6 months' oral administration of chondroitin at the dose of 15 mg/Kg/day is more effective than chondroitin sulphate, and significantly improves the clinical picture, with good regression of the disease.

Skin Biorevitalisation

Skin biorevitalisation by means of intradermal microinjections of hyaluronic acid solutions is one of the most common beauty treatments. The rationale is that the introduction of this polysaccharide into the dermis elicits complex biological responses, mediated by multiple cell signalling activities, which lead to metabolic tissue reactivation. It has been found that intradermal microinjections of chondroitin have biorevitalising effects superior to those of hyaluronic acid. 2 mL of chondroitin at the concentration of 20 or 60 mg/mL was microinjected at fortnightly intervals for 6 months. Another group of subjects was treated similarly with 2 mL of 20 mg/mL hyaluronic acid. Instrumental measurements of trans-epidermal water loss (TEWL), tissue consistency and skin roughness were taken at the beginning and end of the study. The doctor and patient also independently evaluated the overall appearance over time. This study demonstrates that chondroitin, at the same concentration as hyaluronic acid (20 mg/mL), has an earlier and longer-lasting biorevitalising effect, while at higher concentrations (60 mg/mL), the biorevitalising effect of chondroitin is far greater, achieving excellent results as from the second treatment.

Boosting of Activity of Antitumoral Drugs

Chondroitin strongly boosts the apoptotic action of gemcitabine (GEM) and mitomycin-C (MMC), two antitumorals which are useful in the intravesical treatment of non-muscle bladder tumours. In an in vitro study conducted on human bladder cancer cell lines HT-1376, the ability to inhibit the growth and apoptotic/necrotic action of different combinations of GEM or MCC with chondroitin or chondroitin sulphate was evaluated. This study demonstrates that: a) the combination of antitumoral and chondroitin or chondroitin sulphate has a strong effect on inhibition of tumour cell growth; b) the synergistic conditions differ, depending on the antitumoral used; c) polysaccharide-GEM synergism mainly leads to cells that undergo apoptosis, whereas MMC polysaccharide synergism leads to cells that undergo necrosis; d) the synergistic effects of chondroitin are significantly greater than those of chondroitin sulphate; e) the synergistic associations of chondroitin with GEM or MMC can represent a promising therapeutic approach in the field of superficial bladder tumours.

Viscosupplementation and Cartilage Repair

Due to its specificity of action in stimulating chondrocytes and maintaining their cell type over time, chondroitin is an effective agent of viscosupplementation and repair of damaged cartilage tissue. The validity of this therapeutic use of chondroitin was verified by comparing the efficacy of the combination of hyaluronic acid and chondroitin in the treatment of joint diseases connected with damage to the cartilaginous component of the joint with that of a conventional treatment based on hyaluronic acid alone. The study, conducted on volunteers suffering from severe impairment of the knee joint with damage to the cartilaginous component, evident ongoing inflammatory symptoms, swelling and pain, demonstrated that the presence of chondroitin leads to an excellent level of recovery of the joint with repair of the cartilaginous component and a general improvement over time in the pathological picture of the pain symptoms. However, such good results are not observed in conventional viscosupplementation treatment with hyaluronic acid alone.

Treatment of Interstitial Cystitis

The use of hyaluronic acid and chondroitin sulphate in the treatment of interstitial cystitis is known (D. Porru et al., Urol. Int. 1997, 59:26-29; Curtis et al., BUJI, 2008, 103: 56-60; M. Cervigni, Int. Urogynecol., 2008, 19:943-947; D. Porru et al., Reviews on Recent Clinical Trials, 2008, 3:00-00; DE 102006060953). In view of the structural analogies with these polysaccharides and the cell and tissue stimulating actions of chondroitin, a comparative study of the efficacy of combinations of hyaluronic acid and chondroitin or chondroitin sulphate in the treatment of interstitial cystitis was conducted.

The volunteers, with a confirmed diagnosis of interstitial cystitis, were treated with instillations into the catheterised bladder of a solution of hyaluronic acid and chondroitin or hyaluronic acid and chondroitin sulphate. The treatment was repeated once a week for 6 weeks, and then once a month for a further 5 months. At the start of the treatment and at the end of the study a cystoscopy with bladder dilation was performed to check the state of the epithelial tissue, and a bladder wall biopsy was taken to establish the inflammatory state. The urodynamics (urgency, frequency and nocturia) and the presence of stinging and bladder pain were evaluated during the study. Comparison of the cystoscopy performed before and after the treatment demonstrated a general, better resolution of the pathological condition of the patients treated with the hyaluronic acid/chondroitin combination, a finding which was confirmed by the histological evaluation of the bladder wall biopsies, which demonstrated better resolution of the inflammatory process, and by the clinical data, which demonstrated a more complete, faster resolution of the pathological condition, in terms of both urodynamics and residual pain.

Use in Ophthalmic Formulations

Due to its biocompatibility, wound-healing action, hydration capacity, mild antimicrobial action, the optimum viscosity of the aqueous solutions that compose it and the possibility of heat sterilisation without rheological modifications, chondroitin can be used in the manufacture of ophthalmic preparations such as eyedrops and ointments, in combination with other active ingredients. The improved characteristics of eyedrops made with chondroitin as the rheological-therapeutic component are: a) optimum viscosity with no stickiness in the preparation; b) uniform, more homogenous distribution of the eyedrops in all parts of the cornea; c) better stability of the tear film; d) better adhesion to the corneo-conjunctival cells; e) a re-epithelialising, anti-inflammatory and disinfectant action on the corneal surface; f) normalisation of surface tension; g) longer residence time in the cornea; h) the possibility of performing repeated applications during the day to restore adequate tear conditions.

A study of patients suffering from dry eye, which compared two ophthalmic preparations, a conventional one based on hyaluronic acid and one based on chondroitin, both at the concentration of 3% w/v in saline solution, with a therapeutic cycle involving applications 4 times a day for 30 days, demonstrated that eyedrops based on chondroitin present the best evaluation indexes in both the clinical evaluation and the subjective evaluation of the patient treated.

Use in Peritoneal Dialysis

Its physicochemical properties and tissue regeneration capacity form the basis for a novel use of chondroitin in the field of peritoneal dialysis. The dialysis solution mainly consists of sugars (glucose solution) to which other salts are added. Three different concentrations exist (1.36%, 2.27% and 3.86%): the higher the concentration, the greater the quantity of fluids removed. In the event of higher fluid retention the use of solutions with a high concentration will therefore be indicated, whereas in the case of dehydration, solutions with a lower concentration will be more suitable.

If the treatment cannot be optimised, the changeover to haemodialysis must be carefully evaluated.

Peritoneal dialysis has many advantages over haemodialysis, because it involves fewer restrictions on diet and activity, has fewer adverse effects on the haemodynamics, the residual kidney function is better conserved, and rehabilitation is easier. However, a series of drawbacks have emerged in recent years in cases of long-term peritoneal dialysis, associated with deterioration of the peritoneal function, with insufficient removal of water and metabolic waste during dialysis treatment. This deterioration of the peritoneal function is believed to be associated with the high concentrations of glucose present as osmotic agent in peritoneal dialysis fluids, which cause a process of glycosylation of proteins and the formation of reactive oxygen species (ROS). Despite the topicality of the problem and the numerous formulation innovations proposed, strategies have not yet been developed which satisfactorily minimise the functional damage to the peritoneal membrane associated with long-term peritoneal dialysis (US 2010286085, WO 9801141, U.S. Pat. Nos. 5,955,450, and 5,597,8051, WO 9314796, JP 1151462).

It has been found that the use of chondroitin in peritoneal dialysis formulations, as an osmotic agent with a protective effect, represents a good solution for minimising the problems described above, due to the ability of this polysaccharide to promote the regeneration of the peritoneal mesothelium, preventing fibrotic processes.

Treatment of Disorders of the Respiratory System

Chondroitin can be used to treat disorders of the oropharyngeal and pulmonary apparatus of different etiologies such as stomatitis, tonsillitis, laryngitis, pharyngitis, cough and bronchitis due to its rheological and biological properties, such as the ability to retain water, promoting tissue hydration, its film-forming action and ability to adhere to the mucous membranes, its ability to biostimulate cells and tissues, and its anti-inflammatory and antibacterial action. For these uses, chondroitin can be formulated in combination with soothing and mucolytic agents in different pharmaceutical forms such as syrups, tablets, orodispersible powders and sprays.

Chondroitin as a Nutraceutical and Cosmeceutical

In view of the biological activities reported above (especially the anti-inflammatory and antibacterial activity) and its the complete absence of toxicity, chondroitin is useful, possibly together with other compounds, in the formulation of nutraceuticals and cosmeceuticals, which are useful in particular for the biorevitalisation of cells and tissues.

Tissue Growth Scaffolds

Chondroitin can be used as a structural element for the construction of scaffolds for the 3D growth of cell systems for use in the field of regenerative medicine.

The following examples describe the invention in more detail.

EXAMPLE 1

Activation of Keratinocyte Growth

HaCat cells, an immortalised cell line of human keratinocytes, are used as model system. The HaCat cells are grown and amplified in Dulbecco's Modified Eagle Medium (DMEM) containing 10% foetal bovine serum (FBS)+1% Pen-Strep solution (10,000 units of penicillin-G/mL and 10 mg of streptomycin/mL in saline solution) in an incubator for cell cultures (37° C., 5% $CO_2$ in humid air). The wound-healing experiments are conducted by time-lapse optical microscopy, a technique that allows cell behaviour to be monitored for lengthy times (2-4 days) in terms of adhesion, proliferation and motility. The system consists of an inverted optical microscope (Zeiss Axiovert 200), a thermostatic bath (LAUDA Ecoline), a $CO_2$ microincubator with geometry such as to house plates of variable dimensions (from 6 to 96 wells), and a control unit for the output gases (air and $CO_2$). The instrument is also equipped with a digital video camera and a control motor, which allows the incubator to move along directions x, y and z so that the images selected by the operator can be recorded and acquired at pre-set intervals.

The system thus assembled allows the cells to be maintained in an environment that reproduces the optimum conditions for cell growth (atmosphere with 5% v/v of $CO_2$ in humid air and temperature of 37±0.1° C.), and monitored throughout the experiment. The system is also equipped with software which allows accurate analysis of the images. In particular, the instrumentation is equipped with automated software which allows wound repair to be calculated in wound-healing tests and provides data about the repair rate and cell migration rate, which are important parameters for evaluating the biorevitalising effect of substances that can accelerate or inhibit wound repair in vitro.

The standard procedure for a wound-healing test is as follows: a) 100 µL of an 0.1 mg/mL solution of collagen in $CH_3COOH$ is added to each well of a 12-well multiwell plate to increase cell-substrate adhesion and improve the directionality of cell migration, leaving the plate open under a laminar-flow hood until the acid has completely evaporated; b) DMEM 2% FBS is used as culture medium and chondroitin or chondroitin sulphate or hyaluronic acid is added to the wells, the latter being used as comparison systems, with final concentrations of between 0.1 and 1% w/v; nothing is added to the culture medium in two of the 12 wells, which act as controls; c) a portion of the HaCat cell suspension ($1.8*10^5$) is plated in each well to obtain complete confluency after 2 days' incubation (37° C., 5% $CO_2$ in humid air); d) a cut (wound) about 1 mm long is made with a sterile tip in the confluent layer present in each well; e) the 12-well multiwell plate is housed in the incubator stage of the time-lapse video microscopy workstation; f) the experiment only begins when the environmental conditions are ideal for maintenance of the cells in vitro and for a good display of the images (37° C.±0.1, 5% $CO_2$ and absence of condensate); g) 4-5 fields of view of the cut are selected for each well, and the experiment, which lasts for 72-96 h on average, then begins; h) during this period the instrument monitors the closure of the various cuts represented by all the fields of view selected with a time interval of 1 h; i) the wound-healing test is followed by qualitative and quantitative analysis of wound repair by software which automatically measures the area of the cut over time for each field selected; l) the results over time are reported in the form of images, which allow qualitative observation of wound repair, and in numerical terms as the percentage of repair [(time zero area−time t area time zero area)*100].

The results demonstrate that chondroitin already accelerates the repair process at the concentration of 0.1 w/v, whereas chondroitin sulphate slows it. This finding is confirmed more clearly at 1% w/v. The qualitative and quantitative analysis of wound repair shows that the wound is repaired in less than 20 h in the presence of chondroitin, whereas the control only closes after 40 h, and in the case of chondroitin sulphate, the wound does not heal completely, even after 70 h.

EXAMPLE 2

Chondrocyte Proliferation Test

Primary cultures of human chondrocytes isolated from healthy human cartilage samples obtained during rhinoplasty operations were used as model system. The tissue fragments just removed in the operating theatre were immersed in an 0.9% w/w NaCl saline solution and rapidly transferred to the laboratory for extraction of chondrocytes. Operating in sterile conditions under laminar-flow hood, the tissue sample was transferred to a petri dish where it was cut into small pieces using sterile tweezers and scalpels. The pieces of cartilage were then immersed in 0.01M phosphate buffer pH 7.4 (PBS) containing type 1 collagenase (3 mg/mL), dispase (4 mg/mL) and gentamicin (5 µL/mL of an 80 mg/mL solution) to ensure sterility during enzymatic digestion. The pieces were left to incubate overnight in a Falcon tube at 37° C., under stirring. After 16-18 h the solution was filtered through a 70 µm filter, transferring the parts adhering to the Falcon tube onto the filter and washing with 7-8 mL of DMEM 10% FBS. The filtrate was centrifuged at 1,500 rpm for 7 min, the supernatant was removed and the pellet was suspended in 10 mL of DMEM 10% FBS containing fungizone (5 µL/mL of an 80 mg/mL solution) and gentamicin (5 µL/mL of an 80 mg/mL solution). The cell suspension thus obtained was plated in a 25 $cm^2$ flask and incubated at 37° C. in a 5% $CO_2$ atmosphere, with changes of medium every 2 or 3 days until complete confluency of the cell culture. The cells, which have the characteristic appearance of chondrocytes (small swollen cells with a slightly elongated shape), were detached from the base of the flask, counted and incubated again in fresh medium. Starting with 0.4 g of cartilage, about $2*10^6$ cells were generally obtained in the second growth phase. Knowledge of the number of growth cycles to which the culture has previously been subjected is of crucial importance for primary cells; especially in the case of chondrocytes a cell differentiation process is observed wherein, as the growth phases proceed, the cells increasingly present an appearance morphologically similar to fibroblasts. For this reason the entire study is conducted with primary chondrocyte cultures at the 2nd-4th growth phase.

The effect of chondroitin on chondrocyte proliferation was evaluated with time-lapse videomicroscopy, as described in Example 1. The study was performed comparatively with chondrocytes stimulated with chondroitin sulphate, using non-stimulated chondrocytes as control system. $20*10^3$ cells were seeded per well of a 24-well multiwell plate. The cells were treated with chondroitin or chondroitin sulphate with an endotoxin content ≤0.1 EU/mg at a concentration of 1% w/v in DMEM 10% FBS; in the controls, the cells were seeded in DMEM 10% FBS. The experiments were conducted in triplicate and analysed for a total time ranging between 96 and 120 h. Image analysis, conducted with Image Pro-plus 5.1 analysis software, allowed a precise number of cells to be obtained with a manual count at times pre-set by the operator, in order to construct a growth curve over time. The data analysis indicates (Table 2) that the growth of the cells treated with chondroitin was better than that of the untreated cells and the cells treated with chondroitin sulphate.

TABLE 2

Number of chondrocytes as a function of time, incubated in the presence of chondroitin or chondroitin sulphate 1% w/v.

| Time | Cells × $10^4$ | | |
|---|---|---|---|
| (h) | control | chondroitin sulphate | chondroitin |
| 0 | 7.0 ± 0.8 | 7.0 ± 0.5 | 7.0 ± 0.7 |
| 20 | 10.0 ± 1.1 | 10.0 ± 1.2 | 10.2 ± 0.9 |
| 40 | 15.1 ± 1.6 | 14.0 ± 1.8 | 15.3 ± 1.3 |
| 60 | 18.8 ± 1.4 | 18.0 ± 1.6 | 22.0 ± 1.8 |
| 80 | 22.5 ± 1.9 | 21.8 ± 1.7 | 27.0 ± 2.0 |
| 100 | 27.0 ± 2.3 | 25.0 ± 2.5 | 32.0 ± 2.1 |

EXAMPLE 3

Phenotype Analysis with Immunohistochemical Tests on Human Chondrocytes Grown in the Presence of Chondroitin or Sulphated Chondroitin The evaluation of the chondrocyte phenotype of fresh cells extracted from human cartilage tissue samples and after 4, 7 and 10 days' growth in medium containing chondroitin or chondroitin sulphate was conducted with immunohistochemical tests, using the Envision+(DaKo) kit which uses an antibody for type II collagen, considered to be a specific marker for chondrocyte differentiation (Stokes et al., Biochem. J., 2001, 360:461-470). After 4 days' treatment, the various cultures (untreated cells, cells treated with chondroitin and cells treated with chondroitin sulphate) all presented strong positivity to type II collagen, but this condition was only maintained for longer times (7 and 10 days) in the cells treated with chondroitin.

EXAMPLE 4

Analysis by Real-Time PCR of Gene Expression of the Main Specific Markers of Differentiation in Human Chondrocytes Grown in the Presence of Chondroitin or Chondroitin Sulphate To evaluate the biological effects of chondroitin on human chondrocyte cultures, the expression of a set of genes considered key to establishing the phenotype, and suitable markers for evaluating the quality of the tissue generated, was determined. The study was conducted on chondrocytes prepared from human cartilage, as reported in Example 2, the cells being grown in the presence of chondroitin or chondroitin sulphate. Using a standard procedure, $5*10^4$ cells per well were seeded in a 24-well multiwell plate. The chondrocytes were grown in DMEM containing 1% w/v of chondroitin or chondroitin sulphate (endotoxin content ≤0.1 EU/mg). The cells were stimulated for 4, 7 and 10 days (Ishak et al., International J. of Pediatric Otorhinolaryngology, 2011, 75: 835-840), after which the RNA was extracted with Trizol Reagent, as described in the kit manual (Life Technologies Ltd, Milan, Italy). A qualitative morphological analysis of the cell culture was also conducted at the various times, in parallel with RNA extraction, by observing the corresponding samples at 4, 7 and 10 days under the optical microscope. The cells seeded at the three different times were observed under the microscope, and the images that best represented the cell growth conditions were acquired using a time-lapse videomicroscopy workstation. After RNA extraction, reverse transcription was performed with a total of 1 μg RNA and then with amplification by Real-Time PCR of genes which are specific markers for chondrocytes (Table 3).

TABLE 3

Oligo-sequences used for the Real-Time PCR study of the expression of the main specific markers of differentiation in human chondrocytes stimulated with sulphated and non-sulphated chondroitin.

| Gene | Oligo-sequences | Annealing temperature (° C.) |
| --- | --- | --- |
| β-Actin | Forward:<br>5'gCgAgAAgATgA CCC AgA TC 3'<br>Reverse:<br>5'ggATAgCACAgCCTggATAg 3' | 55 |
| Aggrecan | Forward:<br>5' TCgAggACAgCgAggCC 3'<br>Reverse:<br>5' TCgAgggTgTAgCgTgTAgAg 3' | 56 |
| Type I collagen | Forward:<br>5'CAgCCgCTTCACCTACAgC 3'<br>Reverse:<br>5'TTTgTATTCAATCACTgTCTTgCC 3' | 56 |
| Type II collagen | Forward:<br>5'CAACACTgCCAACgTCCAgAT 3'<br>Reverse:<br>5'CTgCTTCgTCCAgATAggCAA 3' | 57 |
| Sox9 | Forward:<br>5'AgACCTTTgggATgCCTTAT 3'<br>Reverse:<br>5' TAgCCTCCCTCACTCCAAgA 3' | 55 |

Genes connected with matrix production, such as aggrecan, type I collagen, type II collagen and the Sox9 gene, the expression of which is closely correlated with the expression of type II collagen, were analysed as specific markers for differentiation and characterisation of chondrocytes. (Akiyama H., Mod Rheumatol., 2008, 18(3): 213-9; Yang et al., J. of Orthopaedic Res. 2011).

The gene expression of said markers on human chondrocytes cultured in basic medium (control) and with chondroitin treatment (C) or chondroitin sulphate treatment (CS) was analysed on cell cultures in the second and third growth phases.

Table 4 shows the values of the gene expression levels after 4, 7 and 10 days compared with the control and with housekeeping genes, which allow the expression to be standardised (ΔΔct method) (Pfaffl M W., Nucleic Acids Res., 2001, May 1; 29(9): e45). The results of the gene expression analysis were reported as the average of at least 3 independent experiments for tests conducted in the presence of C or CS, on cells in phases 2 and 3.

In growth phase 2, aggrecan expression was lower than the control 4 days after plating for the cells treated with C, while at the same time, expression of the gene was slightly higher on average for the cells treated with CS. The difference observed was not significant between the samples treated with CS and the control, but was significant between the samples treated with CS and the samples treated with C. The short-term expression data agreed with the finding of increased chondrocyte proliferation in the presence of C, which may explain the delay in expression, and consequently synthesis, of aggrecan. After 7 days, a significant increase in aggrecan expression was observed in the samples treated with C (1.66±0.22) compared with the control, and slight down-regulation for the samples treated with CS. The latter persisted, becoming significant after 10 days' incubation, whereas at the same time, the aggrecan expression values of the cells treated with C were similar to those of the controls.

Observation in time-lapse experiments of the treated and untreated samples indicated a change of phenotype to the fibroblast type as the culture advanced (and in the subsequent stages), and the evident morphological modification was confirmed by the specific marker, type I collagen. As shown in Table 4, after 4 days' incubation, both treatments (C and CS) led to a non-significant increase in expression of type I collagen; however, after 7 days the increase became significant for the cells treated with CS, unlike the cells treated with C, which actually presented a statistically significant reduction of 30% after long incubation times. Both morphological analysis and evaluation of expression of type I collagen confirmed that the chondrocyte phenotype was better conserved in the presence of C than CS (Chiu L. H. et al., J. Cell. Physiol., 2011, 226: 1981-1988).

Sox9 and type II collagen were also analysed; the latter is considered to be one of the most significant specific markers of the chondrocyte cell type, especially in immunohistochemical typing. The expression of the Sox-9 gene was analysed because Sox-9 was recently classified as a transcription factor that positively controls the synthesis of type II collagen, and is crucial to chondrogenesis (Yang et al., Journal of Orthopaedic Research August 2011).

Similar behaviour was observed for the 2 treatments (C and CS) in relation to up-regulation of Sox9, compared with the control, after 4 days' incubation. Over time (7 and 10 days), chondroitin helped to maintain high levels of expression compared with the control, though with lower significance than at short times, whereas CS exhibited down-regulation after 10 days.

Finally, the main chondrocyte marker, type II collagen, was strongly up-regulated at all the culture times analysed for the treatments with C, and presented a significant increase after short times for the cells treated with CS, which declined as the incubation times increased, substantially returning to the control values.

The panel of genes analysed comparatively demonstrated that treatment with C allows longer maintenance of the phenotype, modulating the production of aggrecan, probably in a way connected with the proliferation stage that precedes the extracellular matrix synthesis stage (Ishak M. F. et al, Journal of Pediatric Otorhinolaryngology, 2011, 75: 835-840). Analysis under the optical microscope of chondrocytes in the third growth phase a few days (4 days) after plating demonstrated that proliferation and matrix production took place. At these times, gene expression of aggrecan in the presence of the C was still low, but then increased compared with the control after 7 days, sequentially with the increase in cell density (Roughley et al., European Cells and Materials, 2006, 11: 1-7). The behaviour in the presence of CS was similar up to 7 days' incubation, but after 10 days there was evident down-regulation, which was significant compared with the expression values of the samples treated with C. When the chondrocytes were in the presence of C, the expression of type I collagen was lower than the control at all incubation times. The results for the medium containing CS were different; it presented an increase in the expression of type I collagen after 7 days. At the same time, for the samples treated with CS, down-regulation of type II collagen was observed in the first 4 days of growth, which was then transformed to overexpression compared with the control (about two-fold) after 7 days and subsequently, with an oscillating trend, further down-regulation after 10 days. 4 days after plating the samples treated with C already presented high expression of type II collagen compared with the control, and this modulation was maintained persistently at 7 and 10 days, confirming the role of this molecule in maintaining the chondrocyte phenotype for a longer time, including in sequential platings.

To sum up, the study as a whole demonstrates that:

a) treatment with C determines a variation in expression of the differentiation and matrix genes analysed (aggrecan, type I collagen, type II collagen and Sox9) at the various analysis times considered (4, 7 and 10 days);

b) the chondrocytes in the second growth phase, if treated with C, present high levels of expression of type II collagen, whereas if they are treated with CS, they present high levels of expression of type I collagen, accompanied by an evident morphological change in fibroblast phenotype;

TABLE 4

Evaluation of expression of aggrecan, type I collagen, Sox 9 and type II collagen, marker genes in human chondrocytes in the second and third growth phases. The data are reported as the ratio of the expression levels of these genes in chondrocyte cultures after 4, 7 and 10 days' treatment with 1% w/v of chondroitin (C) or chondroitin sulphate (CS) compared with the level of expression of the same genes in the control consisting of untreated cells.

| | | | | Fold Expression* | | |
|---|---|---|---|---|---|---|
| Gene | Function | Sample | Phase | 4 g | 7 g | 10 g |
| Aggrecan | This gene is a member of the aggrecan/versican proteoglycan family. The protein encoded is an integral part of the extracellular matrix in the cartilage tissue. | C | II | $0.08 \pm 0.02$ | $1.66 \pm 0.22$ | $1.07 \pm 0.15$ |
| | | | III | $0.16 \pm 0.08$ | $0.79 \pm 0.2$ | $2.3 \pm 1.0$ |
| | | CS | II | $1.28 \pm 0.75$ | $0.72 \pm 0.27$ | $0.45 \pm 0.19$ |
| | | | III | $0.17 \pm 0.10$ | $0.87 \pm 0.20$ | $0.59 \pm 0.13$ |
| Collagen Type I | The gene encoding for the pro-alpha1 chains of type I collagen presents as a formation of collagen fibrils present in connective tissue, and is mainly present in the bones, cornea, dermis and tendons. | C | II | $1.23 \pm 0.29$ | $1.03 \pm 0.52$ | $0.67 \pm 0.20$ |
| | | | III | $0.24 \pm 0.01$ | $0.85 \pm 0.49$ | $0.59 \pm 0.13$ |
| | | CS | II | $1.20 \pm 0.56$ | $1.44 \pm 0.08$ | $1.36 \pm 0.05$ |
| | | | III | $0.34 \pm 0.01$ | $2.42 \pm 0.88$ | $1.09 \pm 0.45$ |
| Collagen Type II | This gene encodes for the alpha-1 chain of type II collagen, a fibrillar protein present in cartilage. Mutations of this gene are associated with the absence of chondrogenesis, chondrodysplasia, and premature osteoarthritis. Specific for the chondrocyte phenotype. | C | II | $2.70 \pm 0.32$ | $2.4 \pm 0.43$ | $2.56 \pm 0.75$ |
| | | | III | $1.69 \pm 0.20$ | $2.62 \pm 0.47$ | $2.3 \pm 0.16$ |
| | | CS | II | $2.8 \pm 0.75$ | $1.25 \pm 0.45$ | $0.58 \pm 0.29$ |
| | | | III | $0.50 \pm 0.01$ | $2.26 \pm 0.17$ | $0.8 \pm 0.45$ |

TABLE 4-continued

Evaluation of expression of aggrecan, type I collagen, Sox 9 and type II collagen, marker genes in human chondrocytes in the second and third growth phases. The data are reported as the ratio of the expression levels of these genes in chondrocyte cultures after 4, 7 and 10 days' treatment with 1% w/v of chondroitin (C) or chondroitin sulphate (CS) compared with the level of expression of the same genes in the control consisting of untreated cells.

| Gene | Function | Sample | Phase | Fold Expression* 4 g | 7 g | 10 g |
|---|---|---|---|---|---|---|
| Sox9 | The SOX9 gene encodes for a protein that plays an important role during the first stages of development. The key role is played above all in the development of the skeleton and cartilage. In the chondrocytes, SOX9 interacts with a specific site on intron 6 of COL2A1, regulating its activity. | C | II | 1.87 ± 0.85 | 1.16 ± 0.15 | 1.78 ± 0.75 |
|  |  |  | III | 3.68 ± 0.44 | 1.09 ± 0.01 | 0.53 ± 0.02 |
|  |  | CS | II | 2.2 ± 1.20 | 0.86 ± 0.31 | 0.53 ± 0.02 |
|  |  |  | III | 2.6 ± 1.21 | 1.41 ± 0.04 | 0.81 ± 0.05 |

*Level of standardised gene expression compared with the control (untreated chondrocytes)

c) the cells in the third growth phase present a lower response to treatment with C or CS, despite the evident persistence of expression of type II collagen in the presence of C, demonstrating that the chondrocyte phenotype is maintained, even in advanced growth phases.

EXAMPLE 5

Molecular Rationales for the Anti-inflammatory Action of Chondroitin

The objective of the study was to evaluate the effects of chondroitin or chondroitin sulphate on gene expression of GRP78 and SOD-2 in human chondrocytes, after treatment with the pro-inflammatory cytokine IL-1β.

Human chondrocytes extracted from nasal cartilage treated with IL-1β, a pro-inflammatory cytokine which acts as mediator in the activation of the biological mechanisms underlying the onset of OA, were used in the study. In particular, the modulation of two markers involved in the manifestation of the inflammatory state, chaperonin GRP78 and the enzyme superoxide dismutase (SOD-2), was evaluated.

In a standard experiment, $10^4$ cells were seeded per well of a 24-well multiwell plate, and after 5 days, when confluency was reached, the cells were starved for 24 hours (incubation in DMEM with 0.5% FBS). The cells were then treated for 2 h with 1% w/v of chondroitin (C) or chondroitin sulphate (CS) (endotoxin content ≤0.1 EU/mg), in DMEM without FBS; the control was maintained under the same conditions, but without the addition of C or CS. IL-1 β at the concentration of 10 ng/mL was then added to the cultures. After 24 h hours' incubation the cells were recovered and the RNA was extracted from them with Trizol Reagent, as described in the kit manual (Life Technologies Ltd, Milan Italy).

Reverse transcription was then performed with a total of 1 μg of RNA, amplifying the reference genes (GRP78 and SOD-2) by Real-Time PCR as reported in Calamia V et al., (Calamia V, et. al., Arthritis Res. Ther. 2010, 12(4):R138).

Table 5 shows the results of the RT-PCR analyses relating to the expression of the two marker genes selected, compared with a negative control consisting of chondrocytes not treated with C, CS or IL-1β and a positive control consisting of chondrocytes treated with IL-1β alone. The expression of GRP78 increased two-fold in the treatment with IL-1β alone (positive control), about three-fold compared with the negative control in the treatment with CS+IL-1β, and about ten-fold in the treatment with C+IL-1β. Although this gene is a symptom of an active inflammatory mechanism, it has been demonstrated that the protein for which it encodes, situated in the endoplasmic reticulum, is an autoantigen of rheumatoid arthritis (a disorder with autoimmune connotations) and is responsible for monocyte stimulation of cytokine synthesis, thus modulating the body's anti-inflammatory response.

As regards the expression of SOD-2 (Table 5), the results demonstrate the substantial equivalence in gene expression in the case of IL-1β+CS and IL-1β, but a considerable reduction in the case of IL-1β+C.

The gene expression values are confirmed by the protein expression data obtained in Western blotting by densitometric analysis of the GRP78 protein bands and SOD2 compared with the constitutive tubulin gene (Table 6)

TABLE 5

Variations in gene expression of GRP78 and SOD 2 in human chondrocytes following treatment with IL-1β, IL-1β chondroitin sulphate (IL-1β CS) and IL-1β + chondroitin (IL-1β + C), compared with the untreated cells taken as 1 (negative control). Gene expression is determined by Real-Time PCR analysis (n = 3, *p < 0.05 IL-1β + CS vs positive control, §p < 0.01 IL-1β + C vs IL-1β + CS and positive control)

| Gene | Control | IL-1β | IL-1β + CS | IL-1β + C |
|---|---|---|---|---|
| GRP78 | 1 | 2.0 ± 0.5 | 2.8 ± 0.2* | 10 ± 2.1§ |
| SOD-2 | 1 | 22 ± 4 | 24 ± 3 | 8 ± 1.1§ |

TABLE 6

Protein expression values of GRP78 and SOD 2 in human chondrocytes following treatment with IL-1β, IL-1β + chondroitin sulphate (IL-1β + CS) and IL-1β + chondroitin (IL-1β + C), obtained from densitometric analysis of Western blotting, analysis conducted on n = 3 independent experiments, *p (blots compared with constitutively expressed tubulin, (*p < 0.05 IL-1β + C vs IL-1β + CS and positive control).

| Protein | Control | IL-1β | IL-1β + CS | IL-1β + C |
|---|---|---|---|---|
| GRP78 | 1 | 1.15 ± 0.15 | 1.18 ± 0.10 | 1.71 ± 0.31* |
| SOD-2 | 1 | 1.96 ± 0.20 | 1.94 ± 0.30 | 1.42 ± 0.22* |

Briefly, the experimental results demonstrate that: a) the expression of GRP78 induced by IL-1β is positively modulated by pre-treatment with C, to a significantly better extent than pre-treatment with CS; b) the process of up-regulation of SOD-2 induced by IL-1β (a symptom of strong oxidative stress) is effectively reduced by pre-treatment with chondroitin, whereas pre-treatment with chondroitin sulphate is ineffective.

EXAMPLE 6

Chondroitin as an Antibacterial

The antibacterial activity of chondroitin (C) and chondroitin sulphate (CS) on the growth of *Escherichia coli* ATCC 25922 and *Enterococcus faecalis* ATCC 19433 on a solid medium in vitro was examined. The concentrations explored ranged from 40 μg/mL to 40 mg/mL of C or CS as final concentrations in the medium. Brain-heart infusion (Oxoid) was used as culture medium for *E. coli* ATCC 25922, and M17 (Oxoid) for *E. faecalis* ATCC 19433; both media were adjusted to the same pH and the same osmolarity before being solidified by adding agar and cooled. 100 μL of a bacterial suspension containing $10^2$, $10^3$ or $10^4$ bacteria/mL was plated as inoculum. The plates inoculated were incubated in shakers in air at 37° C. for 16 h. The number of colonies was then counted on control plates in the absence of the substances under study and on plates at the various concentrations of C and CS. The data from the experiments for the two micro-organisms, conducted in triplicate for each of the conditions, are shown in tables 7 and 8.

The results demonstrate that the effect of C is greater than that of CS at all concentrations, but a strong efficacy of the former emerged in particular, culminating in total inhibition of growth of *E. coli* when 40 mg/mL of C was added, and an upper sensitivity threshold within inhibition which is already high at concentrations 10 times greater

TABLE 7

Inhibition of cell growth of *Escherichia coli* strain ATCC 25922 on plate in the presence of CS and C

| Concentration | No. of bacteria inoculated | | | CFU after 16 h | | | Inhibition factor | Qualitative valuation of inhibition |
|---|---|---|---|---|---|---|---|---|
| Control | 10 | 100 | 1000 | 8 ± 2 | 90 ± 8 | 870 ± 100 | — | |
| 40 μg/mL CS | 10 | 100 | 1000 | 7 ± 2 | 85 ± 7 | 860 ± 70 | 1 | not significant |
| 400 μg/mL CS | 10 | 100 | 1000 | 5 ± 1 | 50 ± 5 | 400 ± 70 | 2 | mild |
| 4 mg/mL CS | 10 | 100 | 1000 | 0 | 9 ± 2 | 100 ± 10 | 10 | significant |
| 40 mg/mL CS | 10 | 100 | 1000 | 0 | 0 | 3 ± 1 | 330 | high |
| 40 μg/mL C | 10 | 100 | 1000 | 7 ± 2 | 80 ± 5 | 800 ± 70 | 1.3 | mild |
| 400 μg/mL C | 10 | 100 | 1000 | 2 ± 1 | 10 ± 2 | 120 ± 30 | 9 | significant |
| 4 mg/mL C | 10 | 100 | 1000 | 0 | 1 ± 1 | 20 ± 4 | 66 | high |
| 40 mg/mL C | 10 | 100 | 1000 | 0 | 0 | 0 | 1000 | total |

TABLE 8

Inhibition of cell growth of *Enterococcus faecalis* strain ATCC 19433 on plate in the presence of CS and C.

| Concentration | No. of bacteria inoculated | | | CFU after 36 h | | | Inhibition factor | Qualitative valuation of inhibition |
|---|---|---|---|---|---|---|---|---|
| Control | 10 | 100 | 1000 | 9 ± 2 | 95 ± 8 | 950 ± 100 | — | |
| 40 μg/mL CS | 10 | 100 | 1000 | 8 ± 2 | 90 ± 7 | 960 ± 70 | — | not significant |
| 400 μg/mL CS | 10 | 100 | 1000 | 7 ± 1 | 80 ± 5 | 780 ± 70 | 1.3 | mild |
| 4 mg/mL CS | 10 | 100 | 1000 | 5 ± 1 | 48 ± 4 | 520 ± 30 | 2 | significant |
| 40 mg/mL CS | 10 | 100 | 1000 | 0 | 15 ± 2 | 120 ± 10 | 7.4 | high |
| 40 μg/mL C | 10 | 100 | 1000 | 8 ± 2 | 82 ± 5 | 870 ± 70 | 1.2 | mild |
| 400 μg/mL C | 10 | 100 | 1000 | 5 ± 1 | 55 ± 6 | 480 ± 30 | 2 | significant |
| 4 mg/mL C | 10 | 100 | 1000 | 0 | 18 ± 4 | 150 ± 4 | 6.1 | significant |
| 40 mg/mL C | 10 | 100 | 1000 | 0 | 0 | 20 ± 2 | 50 | high |

The *Enterococcus* strain proved less sensitive in general; however, in the presence of the maximum concentration of the substances tested it presented an inhibition factor of 7.4 with CS, but a factor of 50 with C. These results demonstrate the efficacy of C as an antibacterial.

EXAMPLE 7

Toxicity Studies on Chondroitin

Acute toxicity study—The study was conducted on two animal models, the mouse and rat, to which chondroitin was administered orally (p.o.) or intravenously (i.v.). For each experiment the animals (mice or Sprague Dawley rats) were divided into 5 groups of 20 (10 males and 10 females) which received p.o. or i.v. chondroitin at doses ranging from 250 to 2,000 mg/Kg for oral administration and 20 to 160 mg/Kg for intravenous administration; the volume administered was 10 mL/Kg for p.o. administration and 5 mL/Kg for i.v. administration. Table 9 shows the study design.

TABLE 9

Study design for evaluation of acute toxicity of chondroitin administered to the mouse and rat in a single oral or intravenous dose.

| Number of animals | Dose (mg/Kg) | Dose (mg/animal) mouse | Dose (mg/animal) rat | Total chondroitin for 20 animals (mg) Mouse | Total chondroitin for 20 animals (mg) Rat |
|---|---|---|---|---|---|
| 20 | 0 | 0.0 | 0 | 0 | 0 |
| 20 | 20 | 0.6 | 4 | 12 | 80 |
| 20 | 40 | 1.2 | 8 | 24 | 160 |
| 20 | 80 | 2.4 | 16 | 48 | 320 |
| 20 | 160 | 4.8 | 32 | 96 | 640 |
| Total | | | | 180 | 1,200 |

During the treatment the animals were examined every 24 h for 40 days, and no signs of toxicity or mortality were observed. At the end of the treatment the animals were euthanized and a complete autopsy was performed. The $LD_{50}$ values for both types of animal were over 2,000 mg/Kg for p.o. administration and 160 mg/Kg for i.v. administration. On the whole, the study demonstrates that chondroitin is non-toxic at the doses used under acute administration conditions.

Subacute toxicity study—The study was performed on the rat by administering chondroitin orally (p.o.) and intramuscularly (i.m.). For each of the two studies the animals (Sprague Dawley rats) were divided into 4 groups formed by 15 males and 15 females; chondroitin at the concentration of 50, 100 and 200 mg/Kg respectively was administered to the first 3 groups, and the carrier alone to the fourth group; the administration volume was 10 mL/Kg for p.o. administration and 5 mL/Kg for i.m. administration. Daily administration continued for 30 days. The doses used represent up to 20 times the human therapeutic dose. The general state of health and behaviour of the treated animals were monitored daily, and weight variations, haematological status and urine were evaluated every 5 days. Throughout the treatment period no deaths occurred, and the animals did not present any significant behavioural alterations or abnormal weight variations. Similarly, the chemico-clinical parameters did not present any statistically significant variations compared with the control animals. At the end of the study all animals were euthanized and an autopsy and histopathological analysis of the main organs (lungs, heart, liver, ovaries, uterus, testicles, kidneys and pituitary gland) were conducted. None of these evaluations indicated any significant differences between the animals treated with chondroitin and the control animals which received the carrier alone. On the whole, the study demonstrates that chondroitin is non-toxic at the doses used under subacute administration conditions.

Chronic toxicity study—This study was conducted on rats (Sprague Dawley) treated daily for 26 weeks with chondroitin administered p.o. (by gavage) at doses ranging from 50 to 200 mg/Kg. The general state of health and behaviour of the treated animals were monitored daily, and weight variations, haematological status and urine were evaluated every 7 days. Throughout the treatment period no deaths occurred, and the animals did not present any significant behavioural alterations or abnormal weight variations. Similarly, the chemico-clinical parameters did not present any statistically significant variations compared with the control animals. At the end of the study all animals were euthanized and an autopsy and histopathological analysis of the main organs (lungs, heart, liver, ovaries, uterus, testicles, kidneys, pituitary gland, lymph nodes and gastrointestinal tract) were conducted. None of these evaluations indicated any significant differences between the animals treated with chondroitin and the control animals which received the carrier alone. On the whole, the study demonstrates that chondroitin is non-toxic at the doses used under chronic administration conditions.

EXAMPLE 8

Mutagenicity and Genotoxicity Studies

The chondroitin mutagenicity studies were conducted on different mutagenicity and genotoxicity models in vitro and in vivo (Sirtori C., File CONDRAL®, Vol. IV—Reproductive Toxicity and Mutagenesis; Slater E. et al., Rapid detection of mutagens and carcinogens, Cancer Res. 1971, 31: 970-973).

In vitro test, Ames' test—The test was performed with and without metabolic activation on 5 strains of *Salmonella typhimurium*. Chondroitin was tested at concentrations of between 2.0 µg/plate and 2.0 mg/plate. Analysis of the reverse mutation obtained at the different doses and in the control did not demonstrate any significant differences in the number of histidine revertants in each group. The study demonstrates that chondroitin and the metabolites it can generate do not induce a specific point-reverse mutation on the strains of *Salmonella typhimurium* tested.

In vitro test, chromosomal aberration test—The chromosomal aberration test was conducted on human lymphocytes in two different experiments with and without metabolic activation. The study design is reported in Table 10.

TABLE 10

Experimental design of chromosomal aberration test for evaluation of the mutagenicity of chondroitin.

| | Without S9 mix | | With S9 mix | |
|---|---|---|---|---|
| | experiment I | experiment II | experiment I | experiment II |
| Exposure period | 4 h | 22 h | 46 h | 4 h | 4 h |
| Recovery | 18 h | — | — | 18 h | 42 h |

TABLE 10-continued

Experimental design of chromosomal aberration test for evaluation of the mutagenicity of chondroitin.

| | Without S9 mix | | With S9 mix | |
|---|---|---|---|---|
| | experiment I | experiment II | experiment I | experiment II |
| Preparation interval | 22 h | 22 h | 46 h | 22 h | 46 h |

Two cultures were analysed in parallel in each of the two experiments. The chondroitin doses tested between 1.6 and 5.0 µg/mL were selected as described in OECD Guideline #473 of 21 Jul. 1997. No significant increases in the number of cells bearing chromosomal aberrations were observed in the double independent study, even at the highest chondroitin concentrations tested.

In vitro test, DNA-repair test—The DNA alteration test was conducted with a strain of *Escherichia coli* sensitive to the action of mutagenic substances. In the study, mitomycin C was used as positive control and penicillin G as negative control. Chondroitin was tested with and without metabolic activation at the concentrations described by Slater et al. (Slater E. et al., Rapid detection of mutagens and carcinogens, Cancer Res. 1971, 31:970-973, 1971. The results demonstrate that even at the highest doses, chondroitin does not interact and does not alter the DNA.

In vivo tests, micronucleus test—Using the mouse as experimental model, chondroitin was administered in an early micronucleus test at doses ranging from 20 to 80 mg/Kg, administered intraperitoneally (i.p.) to 5 groups of Swiss mice (5 per group). The administration was performed twice, 24 h apart, using triethanolamine as positive control. 6 h after the second administration the animals were euthanized, and the bone marrow was prepared as described in the RCC-CCR Study 105303, 2007. The frequency of micronucleated cells was determined on a total of 2,000 erythrocytes per animal. No significant differences were observed in the study between the treated groups and the control which only received the carrier. Taken as a whole, the data demonstrate that chondroitin can be considered non-mutagenic in the early micronucleus test.

EXAMPLE 9

Carcinogenicity Studies

Histopathological examination of the subchronic and chronic tests conducted on the rat (Example 6) demonstrated the total absence of potential neoplastic degeneration in all the fundamental organs. In particular the chronic study, even at the highest doses, demonstrated the total absence of symptoms of irritation of the gastrointestinal tract, which in the long term generally heralds the development of possible tumours, such as gastrointestinal carcinoma. Similarly, it is important to consider that the hydrolytic catabolism of chondroitin is no different from that of chondroitin sulphate, and that the oligosaccharides and sugars obtained represent chemical species naturally present in the body.

EXAMPLE 10

Toxicity Studies on the Reproductive System

Study of fertility and reproductive capacity—The toxicology study of the possible effects of chondroitin on male fertility and female reproductive capacity was conducted on 200 Wistar rats (160 females and 40 males), randomised into four groups, each consisting of 40 females and 10 males, treated with 0, 50, 100 or 200 mg/Kg of chondroitin. Each group of female rats was divided in turn into two sub-groups of 20 animals; the first group received the product daily from the 14th day before the start of the mating period until the 19th day of gestation, and the second received it until the 21st day after the birth. All the males were treated with chondroitin for 60 days before mating and throughout the gestation period of the females. The protocol used follows the guidelines of Directive EEC 85/571. The results did not show any statistically significant differences between the control and the three treated groups, or within each group between the two sub-groups of females and the control. Histopathological analysis of the offspring euthanized after the birth on the 21st day did not show any differences between the control and treated animals, demonstrating the total absence of abnormalities. On the basis of these results it can be concluded that daily oral administration of chondroitin for 60 days, even at the dose of 200 mg/Kg, has no effect on the fertility of male rats; similarly, it has no effect on the reproductive capacity of females treated with chondroitin administered daily up to 200 mg/Kg for 15 days before mating and up to the 21st day of lactation.

Embryo-foetal development—The foetal toxicity study was conducted on 50 pregnant New Zealand rats aged 5 months, randomised into 4 groups of 12 individuals, treated with i.m. chondroitin at the doses of 0, 25, 50 and 100 mg/Kg once a day from the 6th to the 27th day of gestation. On the 28th day the fetuses were removed by caesarian section, and a complete histopathological test was conducted on them. The following parameters were evaluated during the treatment period: increase in body weight of the pregnant mice, number of corpora lutea and implantations, liveborn fetuses, mean weight, gender of liveborn fetuses, number of resorptions and number of stillborn fetuses. The results did not show any statistically significant differences between the treated groups and the control group which received i.m. treatment with the carrier alone. No external alterations or alterations of the skeletal apparatus or viscera were observed in the fetuses in the 4 groups. Overall evaluation of the data leads to the conclusion that chondroitin does not present teratogenic activity, even at the maximum dose tested of 100 mg/Kg.

Postnatal development—The postnatal toxicity study was conducted on 48 female Wistar rats, treated orally from the 15th day of gestation until the end of the lactation period, namely 21 days post-partum. The animals were divided into four groups which received 0, 50, 100 or 200 mg/Kg of chondroitin p.o. every day. At the end of the lactation period all the females were euthanized, and the morphology and skeletal and visceral malformations of the offspring were evaluated. The parameters observed over time were the body weight of the lactating females and the number, gender and weight of the rats born. The results did not show any differences between the treated groups, or between the treated groups and the control group. No abnormalities in the development of the offspring were observed during lactation. It can be concluded that chondroitin has no teratogenic effects in rats after the administration of oral doses of 50, 100 and 200 mg/Kg/day from the 15th day of gestation until the end of the lactation period.

EXAMPLE 11

Sensitisation

The systemic and cutaneous sensitising activity of chondroitin was evaluated on the guinea pig.

Systemic sensitisation and anaphylaxis—The test of chondroitin-induced hypersensitisation was conducted on 6 guinea pigs, as reported below. Six animals were sensitized with an intramuscular injection of 100 µg of ovalbumin+5 mg of chondroitin in 100 µL of saline solution buffered to pH 6.8. The serum was obtained 10 days after the sensitisation of the animals. A further 24 guinea pigs were treated intradermally with the hyperimmune serum of the previously sensitized animals, and divided into 4 groups of 6 (group A: negative control; group B: test with 0.5 mg/mL of chondroitin; group C: test with 50 mg/mL of chondroitin; group D: positive control). 3 h after the intradermal injection with hypersensitized serum, the four groups of animals were treated i.v. as follows: group A: 1 mL of 0.9% NaCl+0.2% of Evans blue solution; group B: 1 mL of 0.5 mg/mL of chondroitin+0.2% Evans blue solution; group C: 1 mL of 50 mg/mL of chondroitin+0.2% Evans blue solution; group D: 1 mL of 0.1 mg/mL of ovalbumin+0.2% of Evans blue solution. 24 h after the i.v. injection of the ovalbumin antigen and Evans blue, all the animals in group D presented exudation of the Evans blue marker in the dermal area in which the hyperimmune serum was injected. However, chondroitin did not induce anaphylactic or hypersensitivity reactions in any of the treated animals.

Skin sensitisation—The test of chondroitin-induced skin hypersensitisation was conducted on guinea pigs, as reported below. 20 animals were sensitized with an intradermal injection of 5.0 mg of chondroitin in 0.1 mL of 0.9% NaCl with and without Freund's adjuvant. 10 animals from the control group received 0.1 mL injections of 0.9% NaCl with and without Freund's adjuvant. Induction of sensitisation was completed after 7 days by applying 0.5 mL of a 50 mg/mL chondroitin solution to the previously injected skin areas of the sensitized animals. 0.5 mL of an 0.9% NaCl solution was applied to the control group. 21 days later, all the animals were treated with 0.5 mL of a 50% chondroitin solution on the left side of the abdomen and 0.5 mL of a 50% NaCl solution on the right side of the abdomen. No sign of skin sensitisation was observed in the treated animals.

EXAMPLE 12

Wound Repair

The mini-pig (an animal weighing 25-28 Kg), a model whose validity for wound-repair studies is widely recognised, was used as experimental model to evaluate the ability of chondroitin to accelerate the repair process of damaged skin tissue. Operating under general anaesthetic from the back of the animals, the hair was shaved and the shaven area was washed thoroughly with a 10% solution of iodine-polyvinylpyrrolidone complex and then with isopropyl alcohol. 12 elliptical wounds, six on each side, 20 mm long and 6 mm wide, were made on the shaven, disinfected backs of the animals. The wounds penetrated as far as the subcutaneous fat, about 4 cm from the median line of the back, with the longer side of the wound parallel to the spinal line. The incisions were then sewn with two stitches to close the dermal plane. The superficial stitches were removed after about 7 days. The wounds were covered with a non-adhesive dressing secured with sticking plaster, and the body of the animals was protected with an elastic bandage. Eight animals were selected and divided into two groups of 4, treated topically with chondroitin (first group) or chondroitin sulphate (second group), as described in the protocol shown in Table 11. Starting from the head of the animal, the first two wounds on both sides were treated with the carrier alone, consisting of 2.5 mL of saline, the second two on both sides were treated with 2.5 mL of a 30 mg/mL solution of chondroitin in saline (first group) or with 2.5 mL of a 30 mg/mL solution of chondroitin sulphate in saline (second group), and the third two on both sides were treated with 2.5 mL of a 60 mg/mL solution of chondroitin in saline (first group) or 2.5 mL of a 60 mg/mL solution of chondroitin sulphate in saline (second group). The treatment was performed by slowly dripping the solution into the wound twice a day and dabbing with a gauze dressing, which was then used to cover the wound so that the active ingredient remained in situ for longer. The study continued for 6 weeks, after which the animals were euthanized. A biopsy of about 4 mm was taken after 4 weeks, while the entire areas of the 12 dorsal wounds were removed from the euthanized animals for histological tests. The following evaluations were performed on the treated animals:

a) an evaluation after 4 and 6 weeks by 4 dermatologists who independently assessed the quality of the wound (colour, texture, edges, distortion) and the appearance of the surrounding tissue on a 5-point scale;

b) a pathological evaluation on a scale of 1 to 3 conducted by two veterinary surgeons on the tissue removed after the animals were euthanized, to evaluate the presence of abnormal histopathological situations (quantity of granulation tissue and inflammatory response, with a score from 3 for optimum healing to 1 for ongoing inflammatory symptoms and abundant granulation tissue);

c) a histological analysis of the 4-week biopsies and the tissue removed after the animals were euthanized, conducted by two histologists operating independently, who evaluated the organisation of the collagen on a 3-point scale. An organisation of the collagen fibres similar to the normal model, but smaller than normal dermis (the best healing), scored 3 points, an intermediate arrangement of the fibre weave scored 2 points, and several fibres arranged in parallel bundles or on a plane scored 1 point.

TABLE 11

Design of study to evaluate the efficacy of chondroitin versus chondroitin sulphate in wound repair. Each group consisted of 4 animals. The first group was treated with chondroitin (C) and the second with chondroitin sulphate (CS).

| Group | First two wounds on both sides irrigated with 2.5 mL of: | Second two wounds on both sides irrigated with 2.5 mL of: | Third two wounds on both sides irrigated with 2.5 mL of: |
|---|---|---|---|
| 1 | Saline | 30 mg/mL of C | 60 mg/mL of C |
| 2 | Saline | 30 mg/mL of CS | 60 mg/mL of CS |

Table 12 shows the wound quality evaluations

TABLE 12

Dermatological, histopathological and histological evaluation of wounds after treatment with chondroitin (C) and chondroitin sulphate (CS); a-b) after 4 and 6 weeks, 4 dermatologists independently evaluated the quality of the wound (colour, texture, edges and distortion) and the appearance of the surrounding tissue on a 5-point scale, where 5 represents excellent quality; b) histopathological evaluation on a scale of 1 to 3 conducted by two veterinary surgeons on the tissue removed after the animals were euthanised, to evaluate the presence of abnormal histopathological situations (quantity of granulation tissue and inflammatory response, where 3 indicates optimum healing and 1 indicates ongoing inflammatory symptoms and abundant granulation tissue; d/e) histological analysis of the 4-week biopsies and tissues removed after the animals were euthanised, conducted by two histologists operating independently, who evaluated the organisation of the collagen on a 3-point scale, where 3 represents an organisation of the collagen fibres similar to the normal model, but smaller than normal dermis (the best healing), 2 represents an intermediate arrangement of the fibre weave, and 1 point represents several fibres arranged in parallel bundles or on a plane.

| | | 30 mg/mL | | 60 mg/mL | |
|---|---|---|---|---|---|
| Evaluation | Saline | C | CS | C | CS |
| a) Evaluation of wound quality after 4 weeks | 2.3 ± 0.1 | 3.8 ± 0.4 | 2.6 ± 0.2 | 4.1 ± 0.3 | 2.9 ± 0.2 |
| b) Evaluation of wound quality after 6 weeks | 3.5 ± 0.3 | 4.5 ± 0.3 | 3.4 ± 0.3 | 4.9 ± 0.1 | 3.7 ± 0.3 |
| c) Histopathological evaluation after 6 weeks | 1.7 ± 0.2 | 2.3 ± 0.1 | 1.7 ± 0.2 | 3.0 ± 0.2 | 2.3 ± 0.2 |
| d) Histological evaluation of biopsies after 4 weeks | 1.3 ± 0.1 | 2.3 ± 0.2 | 1.3 ± 0.1 | 2.7 ± 0.1 | 1.3 ± 0.1 |
| e) Histological evaluation of biopsies after 6 weeks | 1.7 ± 0.2 | 2.7 ± 0.1 | 1.7 ± 0.2 | 3.0 ± 0.2 | 1.7 ± 0.1 |

The dermatological evaluation of wound healing demonstrated a much better quality of the wound-healing process in the presence of chondroitin, which was more rapid and characterised by a qualitatively better appearance of the wound edges and the surrounding tissue.

In the case of treatment with chondroitin, the histopathological evaluation showed a lower content of granulation tissue and very limited inflammatory symptoms.

The histological evaluation demonstrated that in the case of treatment with chondroitin, the organisation of the collagen fibres is very similar to that of normal tissue, indicating a very advanced wound-healing process.

EXAMPLE 13

Therapeutic Potential of Chondroitin in the Treatment of Joint Disease

The therapeutic potential of chondroitin in the treatment of joint disease was evaluated in the dog, an experimental model wherein degenerative or inflammatory orthopaedic problems associated with degenerative joint disease (DJD) are particularly recurrent at both young and geriatric age.

The study was conducted on 90 animals with a mean weight of 30±10 Kg, a mean age of about 8 years, of different breeds, both males and females, all suffering from DJD of the shoulder, hip and/or stifle, randomised into three groups of 30 animals treated with 15 mg/Kg/day of chondroitin (C group), 15 mg/Kg/day of chondroitin sulphate (CS group) or 15 mg/Kg/day of starch (placebo group). The animals received the daily dose with their food. An X-ray and a set of diagnostic tests for DJD were conducted on a preliminary basis on all the animals included in the study. The animals did not receive any pharmacological treatments during the three weeks preceding the study, and during the study did not receive any treatments additional to those tested. The study continued for 6 months; during the treatment, the animals, which were cared for by their owners, were monitored by three veterinary surgeons who independently evaluated the state of the animals. Every month the animals' owners and the three veterinary surgeons filled in a questionnaire, allocating a score on a scale of 1-5 to a set of parameters. Once a month the owners evaluated, on a scale of 1 to 5, the lameness of the animal, its willingness to play, load tolerance, and behaviour indicating pain symptoms. Once a month the veterinary surgeons evaluated, on a scale of 1 to 5, the regression of the disease, the characterisation of the type and degree of joint disease, and the animal's pain and ability to compensate. At the end of the study the state of the disease was verified by an X-ray and a set of diagnostic tests for DJD. On the basis of the questionnaires and the final clinical evaluations, the three veterinary surgeons expressed an average overall score for the regression of the disease in the three groups of animals on a scale of 1 to 10, where values from 3 to 1 indicate increasing deterioration of the clinical symptoms since the start of the trial, and increasing values from 3 to 10 indicate an evolution towards a complete cure. The control group had a mean score of 2.5±1.3, the CS group 5.3±2.3, and the C group 8.5±2.1. Taken as a whole, the trial on dogs suffering from DJD indicates that oral treatment with chondroitin at the daily dose of 15 mg/Kg for 6 months contributes significantly to improving the clinical symptoms, with good regression of the disease.

EXAMPLE 14

Skin Biorevitalisation Treatments Comprising Intradermal Microinjections of Chondroitin Skin biorevitalisation activity resulting from microinjections of chondroitin was evaluated by comparison with similar treatments based on hyaluronic acid. 60 volunteers aged between 50 and 70 years were recruited to the trial, and received aesthetic skin biorevitalisation treatment involving three cycles of fortnightly microinjections in a 6-month period of 2 mL of a pyrogen-free, sterile solution of chondroitin (MW 35 KDa) 20 mg/mL (C-20) or 60 mg/mL (C-60), using a similar conventional treatment cycle with 2 mL of hyaluronic acid 20 mg/mL 1,200 KDa (HA-20) as positive reference. The volunteers had not received similar treatments or chemical peeling treatments in the 5 months immediately preceding the study. During the 6-month treatment period, all the volunteers recruited used the same moisturizing cream, applied morning and evening. Instrumental measurements of TEWL (Trans Epidermal Water Loss) and tissue texture and a silicone replica of the skin surface were performed in the same laboratory at the beginning of the study and after 6 months to document the roughness of the skin. After 0, 2, 4 and 6 months the aesthetic doctor who performed the treatment and the patient independently filled in a questionnaire to evaluate the overall aesthetic situation on a scale of 1 to 5, where 1 indicates that the treatment had no result and 5 indicates complete success. These evaluations, together with the instrumental data, led to an overall evaluation of the result obtained. Table 13 shows the averages of the results obtained.

greater, as regards the evaluations by doctor and patient and the instrumental results, achieving excellent results as from the second treatment.

EXAMPLE 15

Chondroitin as an Agent that Boosts the Activity of Antitumoral Active Ingredients The ability of chondroitin (C) and chondroitin sulphate (CS) to boost the apoptotic action of gemcitabine (GEM) and mitomycin-C(MMC), two antitumorals used in intravesical treatment of non-muscle bladder tumours, was studied. Human bladder cancer cell lines HT-1376 were used as system model, evaluating the ability of different combinations of GEM or MCC and C or CS to inhibit growth.

Human bladder carcinoma cell line HT-1376 (American Type Tissue Cultures Collection, Rockville, Md.) was cultured in DMEM supplemented with heat inactivated 10% foetal bovine serum (FBS), 20 mM 4,2-hydroxyethyl-1-piperazinyl-ethanesulphonic acid (HEPES), 100 U/mL penicillin, 100 pg/mL streptomycin, 1% w/v sodium L-glutamine and 1% w/v pyruvate. The cells were cultured in a humidified atmosphere comprising 95% air/5% $CO_2$ at 37° C. For the study of synergism between C or CS and MMC or GEM in inhibiting the growth of HT-1376, the cells were seeded in 96-well plates at a density of $6*10^3$ cells/well. After 24 hours' incubation at 37° C. the cells were treated with different concentrations of C or CS or GEM or MMC, and polysaccharide-antitumoral combinations thereof. The evaluation of polysaccharide-antitumoral synergism was based on analysis after 72 hours' treatment of the fraction curves of the surviving cells versus the concentration of antitumoral, conducted with the Calcusyn computer program (Biosoft, Ferguson, Mo.). The combination index values (CI) of <1, 1 and >1 indicate synergy, additivity and antagonism respectively in the polysaccharide-antitumoral interaction. The specific contribution of the various ingre-

TABLE 13

60 volunteers aged between 50 and 70 years were recruited to the trial, and received aesthetic skin biorevitalisation treatment involving three cycles of fortnightly microinjections in a 6-month period of 2 mL of a pyrogen-free, sterile solution of chondroitin (MW 35 KDa) 20 mg/mL (C-20) or 60 mg/mL (C-60), using a similar conventional treatment cycle with 2 mL of hyaluronic acid 20 mg/mL 1,200 KDa (HA-20) as positive reference. After 0, 2, 4 and 6 months the aesthetic doctor who performed the treatment and the patient independently filled in a questionnaire to evaluate the overall aesthetic situation on a scale of 1 to 5, where 1 indicates that the treatment had no result and 5 indicates complete success. Instrumental measurements of TEWL (Trans Epidermal Water Loss) and tissue texture and a silicone replica of the skin surface were performed in the same laboratory at the beginning of the study and after 6 months to document the roughness of the skin. Once again, the evaluation was expressed with the opinion of the dermatologist, who evaluated the data comparatively and scored the total result on a scale of 1 to 5. Each figure represents the average of the 10 cases examined.

| | Evaluation | | | | | | | | | | | |
|---|---|---|---|---|---|---|---|---|---|---|---|---|
| | by patient | | | | by doctor | | | | instrumental | | | |
| | | | | | months | | | | | | | |
| Group | 0 | 2 | 4 | 6 | 0 | 2 | 4 | 6 | 0 | 2 | 4 | 6 |
| HA-20 | 1.4 ± 0.1 | 2.8 ± 0.2 | 3.5 ± 0.3 | 4.1 ± 0.3 | 1.3 ± 0.1 | 3.0 ± 0.2 | 4.1 ± 0.1 | 4.3 ± 0.2 | 1.6 ± 0.1 | 3.0 ± 0.2 | 4.0 ± 0.2 | 4.1 ± 0.1 |
| C-20 | 1.2 ± 0.1 | 3.1 ± 0.1 | 4.5 ± 0.2 | 4.5 ± 0.3 | 1.5 ± 0.2 | 3.8 ± 0.4 | 4.5 ± 0.2 | 4.7 ± 0.1 | 1.5 ± 0.2 | 4.1 ± 0.3 | 4.6 ± 0.4 | 4.7 ± 0.1 |
| C-60 | 1.3 ± 0.2 | 4.0 ± 0.5 | 4.9 ± 0.1 | 5.0 ± 0.0 | 1.2 ± 0.1 | 4.0 ± 0.2 | 5.0 ± 0.0 | 5.0 ± 0.0 | 1.1 ± 0.1 | 4.5 ± 0.1 | 5.0 ± 0.0 | 5.0 ± 0.0 |

As will be seen, chondroitin, at the same concentration as hyaluronic acid, has an earlier and longer-lasting biorevitalising effect (HA-20 compared with C-20), while at higher concentrations (C-60), the biorevitalising effect is far dients C, CS, GEM and MMC to the cytotoxicity of the various combinations was determined by calculating the potentiation factor (PF), defined as the ratio between the $IC_{50}$ (50% inhibition of growth) of C, CS, GEM or MMC taken individually and the $IC_{50}$ of the combinations C/GEM, C/MMC, CS/GEM and CS/MMC; a higher PF value indicates greater cytotoxicity.

Flow cytometry was used to evaluate the quantity of apoptotic or necrotic cells. Fluorescein isothiocyanate (Annexin V-FITC) combined with propidium iodide (PI) was used as marker; the apoptotic cells were Annexin V-FITC positive and PI negative, and the necrotic cells were Annexin V-FITC positive and PI positive. The cells were labelled by incubating them with Annexin V-FITC (Diagnostics Med-Systems) and PI (Sigma) in a binding buffer (10 mM HEPES, pH 7.4, 150 mM NaCl, 5 mM KCl, 1 mM $MgCl_2$, 2.5 mM $CaCl_2$) for 10 min at ambient temperature, and then washing and resuspending the cell material in the same buffer. The apoptotic and necrotic cells were analysed by flow cytometry (FACScan, Becton-Dickinson), acquiring an average of $2\times10^4$ events per sample, with determinations in triplicate on three separate experiments.

The effects of C, CS, GEM and MMC, taken individually, on the growth of HT-1376, were evaluated 48 and 72 h after the start of the treatment. All the products caused time- and dose-dependent inhibition of growth. After 72 h, at the concentration of 12 mg/mL, the $IC_{50}$ was 2 mg/mL for C, 12 mg/mL for CS, 18 μ/mL for MMC and 0.5 μ/mL for GEM. At said concentrations the cytotoxic effect was modest, and cell growth resumed if the test product was removed from the medium.

The synergic effect of the polysaccharide-antitumoral combination on inhibition of HT-1376 growth was evaluated on the basis of these results. In particular, the inhibition of growth induced by different concentrations of C or CS combined with MMC or GEM after 72 h was studied, using Calcusyn as data analysis software. The association of C or CS with MMC is strongly synergistic when an excess of polysaccharide over MMC is used, with $IC_{50}$ values of 0.1 and 0.4 for C and CS respectively, which indicate that the synergistic effect of C is better than that of CS. Different behaviour was observed when C or CS was combined with GEM; in this case, there was a synergistic interaction when an excess of GEM over polysaccharide was used. Operating in ratios that give a synergistic interaction (less polysaccharide than antitumoral), $IC_{50}$ values of 0.2 and 0.7 were obtained for C and CS respectively, confirming once again that the synergistic effect of C is better than that of CS.

The synergistic combination of C or CS and GEM was characterised by an important apoptotic effect which was not observed when the active ingredients were used individually, as shown in Table 14.

TABLE 14

Cell state, evaluated with cell sorter, of HT-1376 cells treated for 48 h with 0.04 μg/mL of C or CS and 0.15 μg/mL of GEM, alone or in a polysaccharide-GEM combination.

| Treatment | Cell state | | | |
|---|---|---|---|---|
| | viable | necrotic | apoptotic | |
| | | | early | advanced |
| Not treated | 91 ± 3 | 5 ± 1 | 1 ± 1 | 3 ± 1 |
| C | 59 ± 2 | 28 ± 3 | 6 ± 1 | 7 ± 2 |
| CS | 68 ± 4 | 23 ± 2 | 4 ± 1 | 5 ± 1 |
| GEM | 81 ± 3 | 16 ± 3 | 1 ± 1 | 2 ± 1 |
| C + GEM | 16 ± 2 | 30 ± 2 | 9 ± 2 | 45 ± 6 |
| CS + GEM | 29 ± 2 | 27 ± 4 | 8 ± 1 | 36 ± 5 |

Different behaviour was observed in the case of synergistic combinations of C or CS with MMC (surplus of polysaccharide to antitumoral). In this case, as shown in Table 15, the polysaccharide-antitumoral combination led to extensive cell necrosis, which was greatest in the case of the synergic combination C-MMC.

TABLE 15

Cell state, evaluated with cell sorter, of HT-1376 cells treated for 48 h with 5.7 μg/mL of C or CS and 1.7 μg/mL of MMC, alone or in a polysaccharide-MMC combination.

| Treatment | Cell state | | | |
|---|---|---|---|---|
| | viable | necrotic | apoptotic | |
| | | | early | advanced |
| Not treated | 90 ± 4 | 7 ± 1 | 1 ± 1 | 2 ± 1 |
| C | 56 ± 3 | 41 ± 2 | 1 ± 1 | 2 ± 1 |
| CS | 62 ± 4 | 36 ± 2 | 1 ± 1 | 1 ± 1 |
| MMC | 64 ± 5 | 33 ± 1 | 1 ± 1 | 2 ± 1 |
| C + MMC | 36 ± 2 | 62 ± 3 | 1 ± 1 | 1 ± 1 |
| CS + MMC | 46 ± 1 | 51 ± 2 | 1 ± 1 | 2 ± 1 |

The trial as a whole demonstrates that: a) the combination of antitumoral and C or CS has a strong effect on inhibition of tumour cell growth; b) the synergistic conditions differ, depending on the antitumoral used; c) polysaccharide-GEM synergism mainly leads to cells that undergo apoptosis, whereas MMC polysaccharide synergism leads to cells that undergo necrosis; d) the synergistic effects of C are significantly greater than those of CS; e) the synergistic associations of C with GEM or MMC can represent a promising therapeutic approach in the field of superficial bladder tumours.

EXAMPLE 16

Viscosupplementation and Cartilage Repair

The aim of the study was to evaluate the therapeutic potential of the hyaluronic acid-chondroitin combination (HA-C) in joint disease associated with damage to the cartilaginous component of the joint. The study was conducted on 30 volunteers suffering from severe impairment of the knee joint, with damage to the cartilaginous component, evident ongoing inflammatory symptoms, swelling and pain. The volunteers, aged between 25 and 45 years, of both sexes, were randomised into three groups of 10; the control group was treated with saline, the HA group with hyaluronic acid and the HA-C group with a mixture of hyaluronic acid and chondroitin. The viscosupplementation treatment was performed 3 times at 2-month intervals by injecting into the joint 2 mL of a sterile, pyrogen-free solution consisting of a saline solution (0.9% NaCl) for the control group, a 20 mg/mL solution of hyaluronic acid 1,200 KDa for the HA group and a 20 mg/mL solution of hyaluronic acid 1,200 KDa+20 mg/mL of chondroitin for the HA-C group. Before and at the end of the 6-month study the volunteers underwent an X-ray and MRI scan of the joint. Three orthopaedic surgeons independently evaluated the development of the pathological symptoms (pain, inflammatory state and swelling), and repair of cartilage damage, over time (before treatment, and after 3 and 6 months), on a scale of 1 to 5 (where 1 represents absence of healing, and 5 indicates total remission of the pathological symptoms and complete repair of the damage to the cartilage tissue). Table 16 shows the concluding data of the study. Said data demonstrates that, in viscosupplementation treatments with cartilage damage, the presence of chondroitin leads to an excellent level of repair of the cartilaginous component of the joint and a general improvement in pathological symptoms over time.

TABLE 16

The viscosupplementation treatment was performed 3 times at 2-month intervals by injecting into the joint 2 mL of a sterile, pyrogen-free solution consisting of a saline solution (0.9% NaCl) for the control group, a 20 mg/mL solution of hyaluronic acid 1,200 KDa for the HA group and a 20 mg/mL solution of hyaluronic acid 1,200 KDa + 20 mg/mL of chondroitin for the HA-C group. Three orthopaedic surgeons independently evaluated the development of the pathological symptoms (pain, inflammatory state and swelling), and repair of cartilage damage, over time (before treatment, and after 3 and 6 months), on a scale of 1 to 5 (where 1 represents absence of healing, and 5 indicates total remission of the pathological symptoms and complete repair of the damage to the cartilage tissue). The values reported are the average of the 3 independent evaluations.

| | Pain | | | Inflammation | | | Swelling | | | Cartilage repair | | |
|---|---|---|---|---|---|---|---|---|---|---|---|---|
| | | | | | Months | | | | | | | |
| Group | 0 | 3 | 6 | 0 | 3 | 6 | 0 | 3 | 6 | 0 | 3 | 6 |
| Control | 1.0 ± 0.1 | 1.3 ± 0.2 | 1.3 ± 0.1 | 1.5 ± 0.2 | 1.0 ± 0.2 | 1.4 ± 0.1 | 1.5 ± 0.2 | 1.0 ± 0.1 | 1.8 ± 0.2 | 1.0 ± 0.1 | 1.5 ± 0.2 | 1.6 ± 0.1 |
| HA | 1.6 ± 0.2 | 3.1 ± 0.4 | 4.0 ± 0.3 | 1.3 ± 0.2 | 3.1 ± 0.2 | 4.1 ± 0.5 | 1.2 ± 0.1 | 3.1 ± 0.3 | 4.20.5 | 1.0 ± 0.1 | 1.5 ± 0.2 | 1.4 ± 0.3 |
| HA-C | 1.5 ± 0.1 | 3.5 ± 0.4 | 5.0 ± 0.0 | 1.6 ± 0.2 | 4.1 ± 0.4 | 5.0 ± 0.0 | 1.4 ± 0.2 | 4.2 ± 0.2 | 5.0 ± 0.0 | 1.1 ± 0.1 | 3.2 ± 0.5 | 5.0 ± 0.0 |

EXAMPLE 17

Chondroitin in the Treatment of Interstitial Cystitis 10 women aged between 35 and 60 years, with a confirmed diagnosis of non-ulcerative interstitial cystitis based on urodynamic, clinical and endoscopic parameters, the latter exhibiting the presence of haemorrhagic petechiae in the cystoscopy with bladder distension, were recruited to the study. The subjects were randomised into 2 groups of 5 individuals; the first group was treated by instillation into the bladder through a catheter of a solution (40 mL) containing 40 mg of hyaluronic acid MW 1.800 KDa (HA) and 40 mg of chondroitin sulphate (CS), and the second with a solution (40 mL) containing 40 mg of hyaluronic acid MW 1.800 KDa (HA) and 40 mg of chondroitin (C). This treatment was repeated weekly for 6 weeks and then monthly for a further 5 months. At the start of the treatment and at the end of the study a cystoscopy with bladder distension was performed to verify the state of the epithelial tissue, and a bladder wall biopsy was taken to establish the inflammatory state. Before and 2, 5 and 7 months after the treatment, the urologist filled in a clinical form, by agreement with the patient, to quantify the urodynamics (urgency, frequency and nocturia) and the presence of stinging and bladder pain. All parameters were evaluated on a scale of 0 to 6, where 0 indicates the absence of pathological symptoms. Table 17 shows the data obtained.

Comparison of the cystoscopy with bladder distension performed before and after the treatment demonstrated a general, better resolution of the pathological condition of the patients in the HA-C group than the HA-CS group, a finding which was confirmed by the histological evaluation of the bladder wall biopsies, which demonstrated better resolution of the inflammatory process in the HA-C group than the HA-CS group. The clinical data reported in Table 11 are also consistent with this evaluation, demonstrating a more complete, faster resolution of the pathological symptoms for the HA-C group in urodynamic terms and as regards residual pain.

TABLE 17

10 female volunteers suffering from non-ulcerative interstitial cystitis were randomised into 2 groups of 5 individuals; the first group (HA-C) was treated by instillation into the bladder, through a catheter, of a solution (40 mL) containing 40 mg of hyaluronic acid MW 1.800 KDa (HA) and 40 mg of chondroitin sulphate (CS), and the second group (HA-CS) with a solution (40 mL) containing 40 mg of hyaluronic acid MW 1.800 KDa (HA) and 40 mg of chondroitin (C). This treatment was repeated weekly for 6 weeks and then monthly for a further 5 months. Before and 2, 5 and 7 months after the treatment, the urologist filled in a clinical form, by agreement with the patient, to quantify the urodynamics (urgency, frequency and nocturia) and the presence of stinging and bladder pain. All parameters were evaluated on a scale of 0 to 6, where 0 indicates the absence of pathological symptoms.

| Time | urgency | | frequency micturition | | nocturia | | stinging | | pain bladder | |
|---|---|---|---|---|---|---|---|---|---|---|
| (months) | HA-C | HA-CS | HA-C | HA-CS | HA-C | HA-CS | HA-C | HA-CS | HA-C | HA-CS |
| 0 | 5.7 ± 0.2 | 5.8 ± 0.3 | 5.7 ± 0.2 | 5.9 ± 0.1 | 5.8 ± 0.2 | 5.7 ± 0.1 | 5.9± | 5.8 ± 0.2 | 5.7 ± 0.3 | 5.7 ± 0.2 |
| 2 | 2.4 ± 0.4 | 4.4 ± 0.2 | 2.1 ± 0.3 | 3.2 ± 0.3 | 2.0 ± 0.6 | 3.5 ± 0.3 | 2.4 ± 0.1 | 4.3 ± 0.3 | 1.8 ± 0.2 | 3.7 ± 0.3 |
| 5 | 1.3 ± 0.1 | 3.2 ± 0.3 | 0.9 ± 0.2 | 2.4 ± 0.4 | 1.3 ± 0.2 | 3.1 ± 0.1 | 0.9 ± 0.1 | 3.0 ± 0.3 | 0.7 ± 0.1 | 2.6 ± 0.1 |
| 7 | 1.1 ± 0.1 | 2.6 ± 0.3 | 0.9 ± 0.1 | 1.9 ± 0.2 | 1.0 ± 0.1 | 2.8 ± 0.2 | 0.5 ± 0.1 | 2.6 ± 0.2 | 0.6 ± 0.3 | 2.1 ± 0.1 |

EXAMPLE 18

Ophthalmic Formulations

Two ophthalmic preparations were compared: a conventional one based on hyaluronic acid and one based on chondroitin, both at the concentration of 3% w/v in NaCl saline solution at pH 7.4. The eyedrops were prepared in single-dose packaging sterilised in the autoclave.

The study was conducted on 30 volunteers suffering from dry eye, to whom the eyedrops were administered 4 times a day for 30 days. The volunteers, of both sexes, aged between 45 and 60 years, were randomised into two groups of 15, and treated with the two types of eyedrops. Under medical control the inflammatory state of the corneal surface was evaluated at the beginning and end of the treatment, and the evaluations of the treated patients relating to tolerability, duration of the wetting effect, and visual alteration after application, were recorded. A scale of 1 to 5 was used for the clinical evaluations and the patients' evaluations, where 5 represents optimum resolution of the pathological condition and its sequelae.

As demonstrated by the experimental results reported in Table 18, the eyedrops based on chondroitin (C) presented the best evaluation indexes on both clinical evaluation and subjective evaluation by the treated patients.

TABLE 18

The study was conducted on 30 volunteers of both sexes aged 45 to 60, suffering from dry eye. The volunteers were randomised into two groups of 15, to which eyedrops were administered 4 times a day for 30 days. The first group (HA) was treated with eyedrops based on 3% w/v hyaluronic acid in NaCl saline solution at pH 7.4. The second group (C) was treated with eyedrops based on 3% w/v chondroitin in NaCl saline solution at pH 7.4. The eyedrops were prepared in single-dose packaging sterilised in the autoclave.

| Time | Doctor | | Patient | | | | | |
|---|---|---|---|---|---|---|---|---|
| | corneal inflammation | | tolerability | | wetting effect | | absence of visual alteration | |
| (days) | HA | C | HA | C | HA | C | HA | C |
| 0 | 1.0 ± 0.1 | 1.1 ± 0.2 | — | — | — | — | — | — |
| 10 | — | — | 3.8 ± 0.2 | 4.7 ± 0.2 | 4.0 ± 0.2 | 4.8 ± 0.3 | 3.5 ± 0.2 | 4.6 ± 0.2 |
| 20 | — | — | 3.7 ± 0.3 | 4.5 ± 0.5 | 4.1 ± 0.3 | 4.6 ± 0.2 | 3.2 ± 0.1 | 4.7 ± 0.1 |
| 30 | 3.5 ± 0.2 | 4.2 ± 0.3 | 3.9 ± 0.3 | 4.8 ± 0.1 | 4.4 ± 0.3 | 4.9 ± 0.1 | 3.6 ± 0.2 | 4.8 ± 0.1 |

Under medical control the inflammatory state of the corneal surface was evaluated at the beginning and end of the treatment, and the evaluations of the treated patients relating to tolerability, duration of the wetting effect, and visual alteration after application, were recorded. A scale of 1 to 5 was used for the clinical evaluations and the patients' evaluations, where 5 represents optimum resolution of the pathological condition and its sequelae.

EXAMPLE 19

Protective Effect of Chondroitin in Intraperitoneal Dialysis Solutions

The objective of the study was to evaluate peroxidative damage in the peritoneal membrane associated with the presence of glucose, chondroitin or chondroitin sulphate in peritoneal dialysis fluids. The peroxidative effect of lipids in the peritoneal tissue following repeated peritoneal dialysis treatments was evaluated using as experimental model 8-week-old male Wistar rats treated with 4 types of formulation: a) glucose 2.5% w/v, chondroitin sulphate MW 20-40 KDa 0.1% w/v, sodium 135.0 mEq/L, magnesium 1.5 mEq/L, calcium 4.0 mEq/L, chlorine 105.5 mEq/L, lactic acid 35.0 mEq/L, pH 7.0-7.3, $\pi$ solution/$\pi$ saline 1.4-1.6; b) glucose 2.5% w/v, chondroitin MW 20-40 KDa 0.1% w/v, sodium 135.0 mEq/L, magnesium 1.5 mEq/L, calcium 4.0 mEq/L, chlorine 105.5 mEq/L, lactic acid 35.0 mEq/L, pH 7.0-7.3, $\pi$ solution/$\pi$ saline 1.4-1.6; c) chondroitin sulphate MW 20-40 KDa 2.5% w/v, sodium 135.0 mEq/L, magnesium 1.5 mEq/L, calcium 4.0 mEq/L, chlorine 105.5 mEq/L, lactic acid 35.0 mEq/L, pH 7.0-7.3, with the addition of NaCl until the $\pi$ solution/$\pi$ saline ratio was in the 1.4-1.6 range; d) chondroitin sulphate MW 20-40 KDa 2.5% w/v, sodium 135.0 mEq/L, magnesium 1.5 mEq/L, calcium 4.0 mEq/L, chlorine 105.5 mEq/L, lactic acid 35.0 mEq/L, pH 7.0-7.3, with the addition of NaCl until the $\pi$ solution/$\pi$ saline ratio was in the 1.4-1.6 range; 40 animals were randomised into 4 groups of 10, and 15 mL of solution was injected into the peritoneal cavity of each animal under ether anaesthesia for 10 consecutive days. At the end of the study the peritoneum of the euthanized animals was removed, and lipid peroxidation was evaluated quantitatively on the tissue by the thiobarbituric acid (TBA) method, using the OxiSelect TBARS Assay Kit (Cell Biolabs Inc.). Lipid peroxidation is a well-known cell damage mechanism. Lipid peroxides are unstable indicators of oxidative stress of the cells which, as they decompose, form reactive compounds like malonyldialdehyde (MDA), the main marker for lipid peroxidation. The kit used provides a simple, reproducible system for assaying MDA, and consequently lipid oxidation, in tissue homogenate samples, based on the ability of MDA to form a 1:2 complex with thiobarbituric acid (TBARS—Thiobarbituric Acid Reactive Substances) which can be determined spectrophotometrically. The kit contains an MDA standard to be used as positive control and for the calibration curves. The MDA contained in the samples and the MDA standard were reacted with TBA with a short incubation at 95° C., which leads to formation of the TBARS complex, determined quantitatively and spectrophotometrically by comparison with the standard curve. The fresh peritoneal tissue samples were washed repeatedly with a heparin solution containing PBS to remove the haemoglobin, suspended (100 mg/mL) in PBS containing a 1× solution of BHT (provided in the kit to prevent further oxidation of the lipids during processing of the samples), and then homogenised in ice and centrifuged at 10,000 rpm for 5 min, collecting the supernatant on which the TBARS level was assayed. Taking as 1 the value of the lipid peroxides/g of tissue in the treatment with solution a) containing 2.5% w/v of glucose and 0.1% w/v of chondroitin sulphate, the corresponding value obtained with solution b) containing 2.5% w/v glucose and 0.1% w/v chondroitin was 0.7, while the value obtained with solution c) containing 2.5% w/v of chondroitin sulphate was 0.5, and the value obtained with solution d) containing 2.5% w/v of chondroitin was 0.1. These data demonstrate that in intraperitoneal dialysis chondroitin can be used as osmotic agent instead of glucose, with excellent results in terms of protection of the peritoneal tissue against lipid peroxidation stress in systematic intraperitoneal dialysis; however, an equally satisfactory result cannot be obtained by using chondroitin sulphate with similar molecular weight characteristics.

The invention claimed is:

1. Pharmaceutical, nutraceutical, cosmeceutical compositions or medical devices in a form selected from the group consisting of capsules, tablets, eye drops, gel, creams, solutions or suspensions, mouth soluble powders, spray and syrups, said compositions comprising non sulphated chondroitin and hyaluronic acid as the active ingredient.

2. Compositions according to claim 1 further comprising other active ingredients.

3. Compositions according to claim 1 for use selected from the group consisting of wound repair, treatment of articular, ocular, oncological pathologies, pathologies of the respiratory apparatus, osteoarthritis, interstitial cystitis, cutaneous senescence, osmotic and protective agent in solutions for intraperitoneal dialysis and scaffold for the growth of 3D cell cultures.

4. Compositions according to claim 3 for use selected from the group consisting of articular viscosupplementation and repair of cartilaginous tissue, cutaneous biorivitalizazion by means of intradermal microinjections, treatment of dry eye disease and application of contact lenses.

* * * * *

SEQUENCE LISTING

<160> NUMBER OF SEQ ID NOS: 10

<210> SEQ ID NO 1
<211> LENGTH: 20
<212> TYPE: DNA
<213> ORGANISM: Unknown
<220> FEATURE:
<223> OTHER INFORMATION: Artificial sequence hybridizing with human chondrocyte beta actin

<400> SEQUENCE: 1
gcgagaagat gacccagatc                                               20

<210> SEQ ID NO 2
<211> LENGTH: 20
<212> TYPE: DNA
<213> ORGANISM: Unknown
<220> FEATURE:
<223> OTHER INFORMATION: Artificial sequence hybridizing with human chondrocyte beta actin

<400> SEQUENCE: 2
ggatagcaca gcctggatag                                               20

<210> SEQ ID NO 3
<211> LENGTH: 17
<212> TYPE: DNA
<213> ORGANISM: Unknown
<220> FEATURE:
<223> OTHER INFORMATION: Artificial sequence hybridizing with human chondrocyte aggrecan

<400> SEQUENCE: 3
tcgaggacag cgaggcc                                                  17

<210> SEQ ID NO 4
<211> LENGTH: 21
<212> TYPE: DNA
<213> ORGANISM: Unknown
<220> FEATURE:
<223> OTHER INFORMATION: Artificial sequence hybridizing with human chondrocyte Aggrecan

<400> SEQUENCE: 4
tcgagggtgt agcgtgtaga g                                             21

<210> SEQ ID NO 5
<211> LENGTH: 19
<212> TYPE: DNA
<213> ORGANISM: Unknown
<220> FEATURE:
<223> OTHER INFORMATION: Artificial sequence hybridizing with human chondrocyte type I collagen

<400> SEQUENCE: 5
cagccgcttc acctacagc                                                19

<210> SEQ ID NO 6
<211> LENGTH: 24
<212> TYPE: DNA
<213> ORGANISM: Unknown
<220> FEATURE:
<223> OTHER INFORMATION: Artificial sequence hybridizing with human chondrocyte type I collagen

<400> SEQUENCE: 6
tttgtattca atcactgtct tgcc                                          24

```
<210> SEQ ID NO 7
<211> LENGTH: 21
<212> TYPE: DNA
<213> ORGANISM: Unknown
<220> FEATURE:
<223> OTHER INFORMATION: Artificial sequence hybridizing with human
      chondrocyte type II collagen

<400> SEQUENCE: 7
caacactgcc aacgtccaga t                                              21

<210> SEQ ID NO 8
<211> LENGTH: 21
<212> TYPE: DNA
<213> ORGANISM: Unknown
<220> FEATURE:
<223> OTHER INFORMATION: Artificial sequence hybridizing with human
      chondrocyte type II collagen

<400> SEQUENCE: 8
ctgcttcgtc cagataggca a                                              21

<210> SEQ ID NO 9
<211> LENGTH: 20
<212> TYPE: DNA
<213> ORGANISM: Unknown
<220> FEATURE:
<223> OTHER INFORMATION: Artificial sequence hybridizing with human
      chondrocyteSOX9

<400> SEQUENCE: 9
agacctttgg gatgccttat                                                20

<210> SEQ ID NO 10
<211> LENGTH: 20
<212> TYPE: DNA
<213> ORGANISM: Unknown
<220> FEATURE:
<223> OTHER INFORMATION: Artificial sequence hybridizing with human
      chondrocyte SOX9n

<400> SEQUENCE: 10
tagcctccct cactccaaga                                                20
```